United States Patent
Mori et al.

(10) Patent No.: US 7,811,758 B2
(45) Date of Patent: Oct. 12, 2010

(54) METHOD AND APPARATUS OF AUTOMATICALLY ISOLATING AND PURIFYING NUCLEIC ACID

(75) Inventors: Toshihiro Mori, Asaka (JP); Yoshihiko Makino, Asaka (JP)

(73) Assignee: Fujifilm Corporation, Tokyo (JP)

( * ) Notice: Subject to any disclaimer, the term of this patent is extended or adjusted under 35 U.S.C. 154(b) by 1008 days.

(21) Appl. No.: 11/547,093

(22) PCT Filed: Mar. 28, 2005

(86) PCT No.: PCT/JP2005/006530

§ 371 (c)(1),
(2), (4) Date: Sep. 29, 2006

(87) PCT Pub. No.: WO2005/093053

PCT Pub. Date: Oct. 6, 2005

(65) Prior Publication Data

US 2008/0275228 A1    Nov. 6, 2008

(30) Foreign Application Priority Data

Mar. 29, 2004    (JP)    ............... 2004-094396

(51) Int. Cl.
  *C12Q 1/68*    (2006.01)
  *C12M 1/34*    (2006.01)
  *C07H 21/00*    (2006.01)
(52) U.S. Cl. .................. 435/6; 435/283.1; 536/22.1; 536/25.4
(58) Field of Classification Search .............. 435/6, 435/283.1; 536/22.1, 25.4
See application file for complete search history.

(56) References Cited

U.S. PATENT DOCUMENTS 3,647,390 A    3/1972    Kubodera et al.

(Continued)

FOREIGN PATENT DOCUMENTS

DE    19 33 846 A1    1/1970

(Continued)

*Primary Examiner*—Stephen Kapushoc
*Assistant Examiner*—Narayan K Bhat
(74) *Attorney, Agent, or Firm*—Birch, Stewart, Kolasch & Birch, LLP

(57) ABSTRACT

A method of automatically isolating and purifying nucleic acid from a nucleic acid-containing specimen is provided, the method comprising: injecting a liquid into a cartridge for isolation and purification of a nucleic acid including at least two openings from one opening of the at least two openings, in which the cartridge includes a container having the at least two openings and containing a nucleic acid-adsorbent solid phase; passing the liquid through the nucleic acid-adsorbent solid phase by a pressure difference generated by a pressure generation means for generating a pressure difference between the inside and outside of the container; and discharging the liquid from the other opening of the container to the outside of the container by a pressure difference generated by the pressure generation means, wherein a pressure generated in the inside of the container by the pressure generation means is measured, a pressure change velocity and a pressure change acceleration are calculated on the basis of the value of the measured pressure, and the timing of completion of discharge of the liquid from the container is determined by use of a temporal change pattern of at least one of the measured pressure, the pressure change velocity and the pressure change acceleration.

3 Claims, 13 Drawing Sheets

U.S. PATENT DOCUMENTS

| | | | | |
|---|---|---|---|---|
| 4,769,153 A | * | 9/1988 | Allington | 210/656 |
| 5,760,299 A | | 6/1998 | Johnson et al. | |
| 6,136,555 A | * | 10/2000 | Jones | 435/41 |
| 6,370,942 B1 | * | 4/2002 | Dunfee et al. | 73/37 |
| 2003/0170664 A1 | * | 9/2003 | Mori et al. | 435/6 |

FOREIGN PATENT DOCUMENTS

| | | |
|---|---|---|
| JP | 7-51065 A | 6/1995 |
| JP | 9-179603 A | 7/1997 |
| JP | 10-19883 A | 1/1998 |
| JP | 11-333258 A | 12/1999 |
| JP | 2003-128691 A | 5/2003 |
| WO | WO-89/09265 A1 | 10/1989 |
| WO | WO-97/26532 A1 | 7/1997 |

* cited by examiner

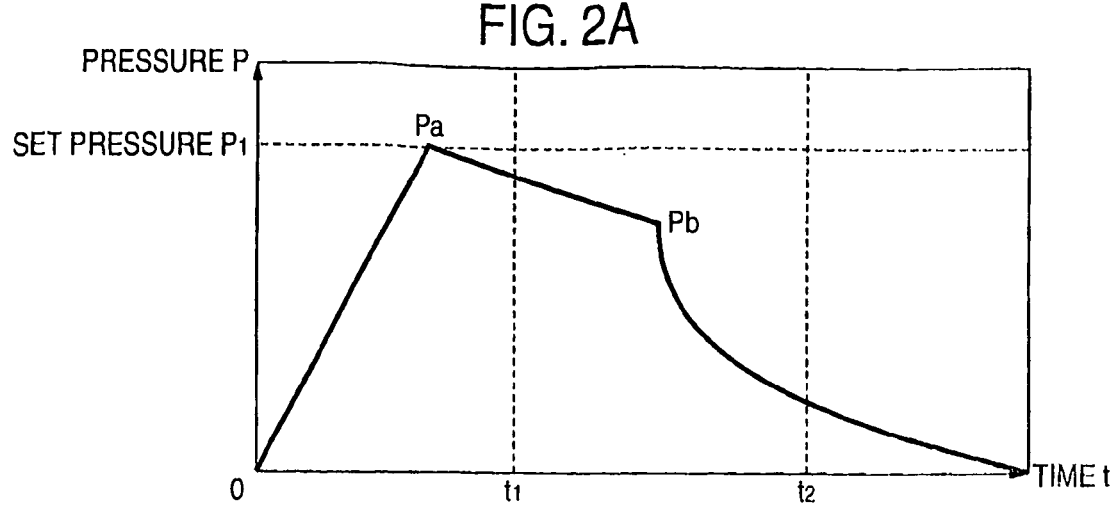
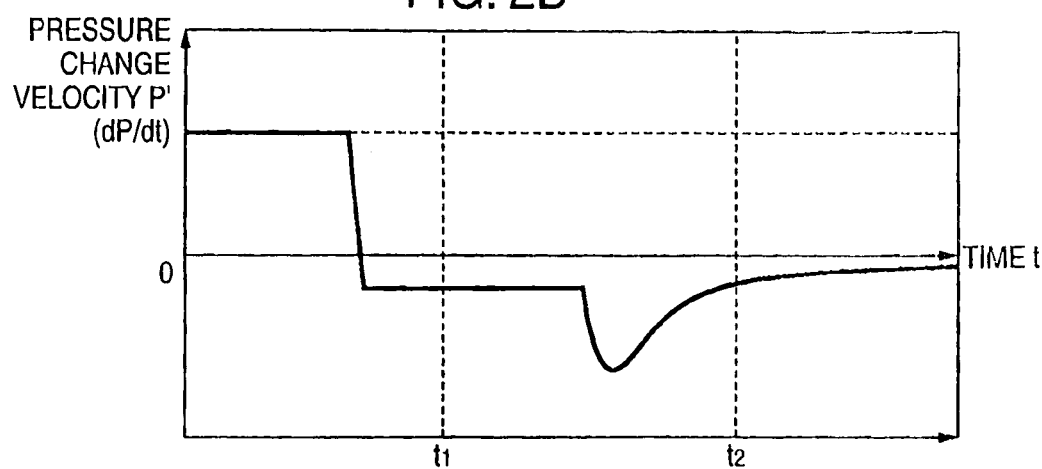
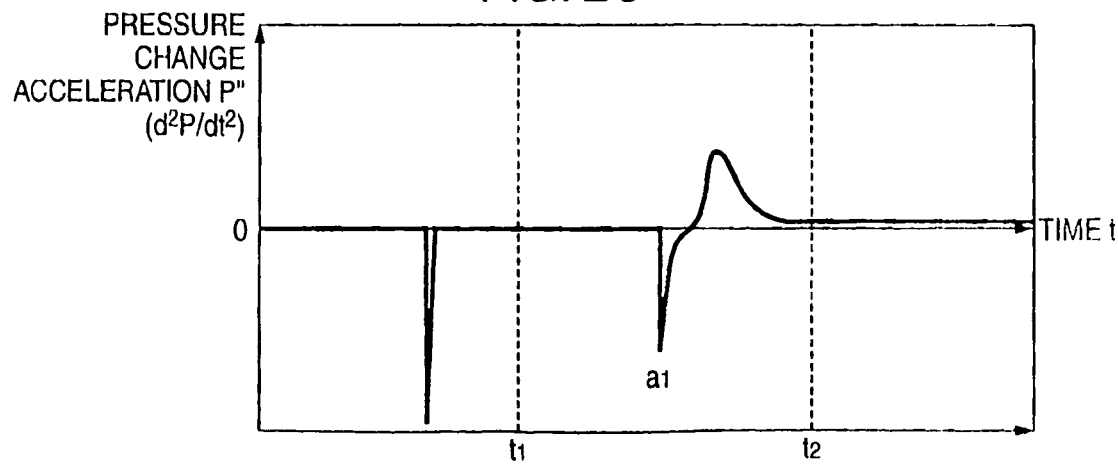

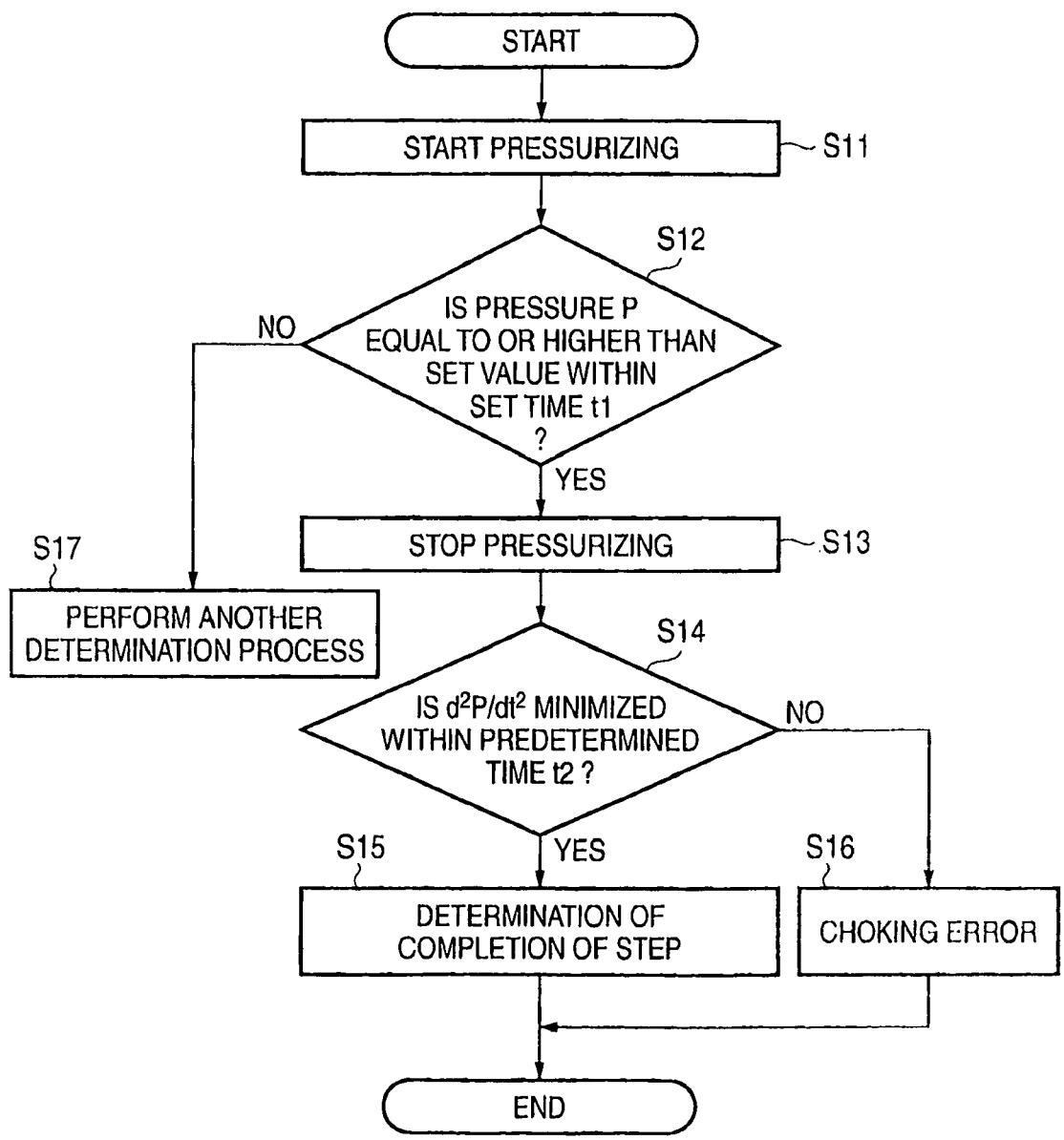

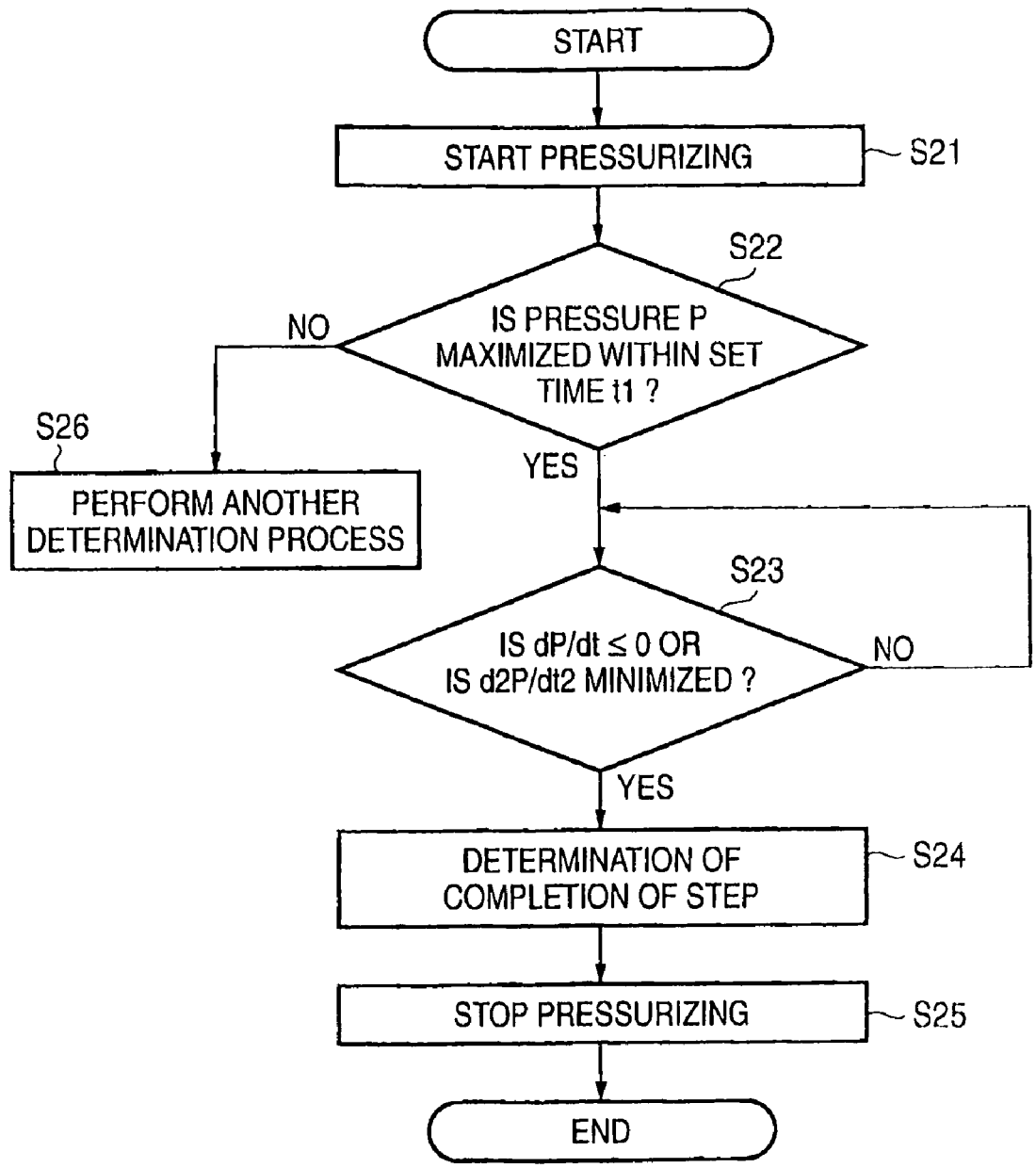

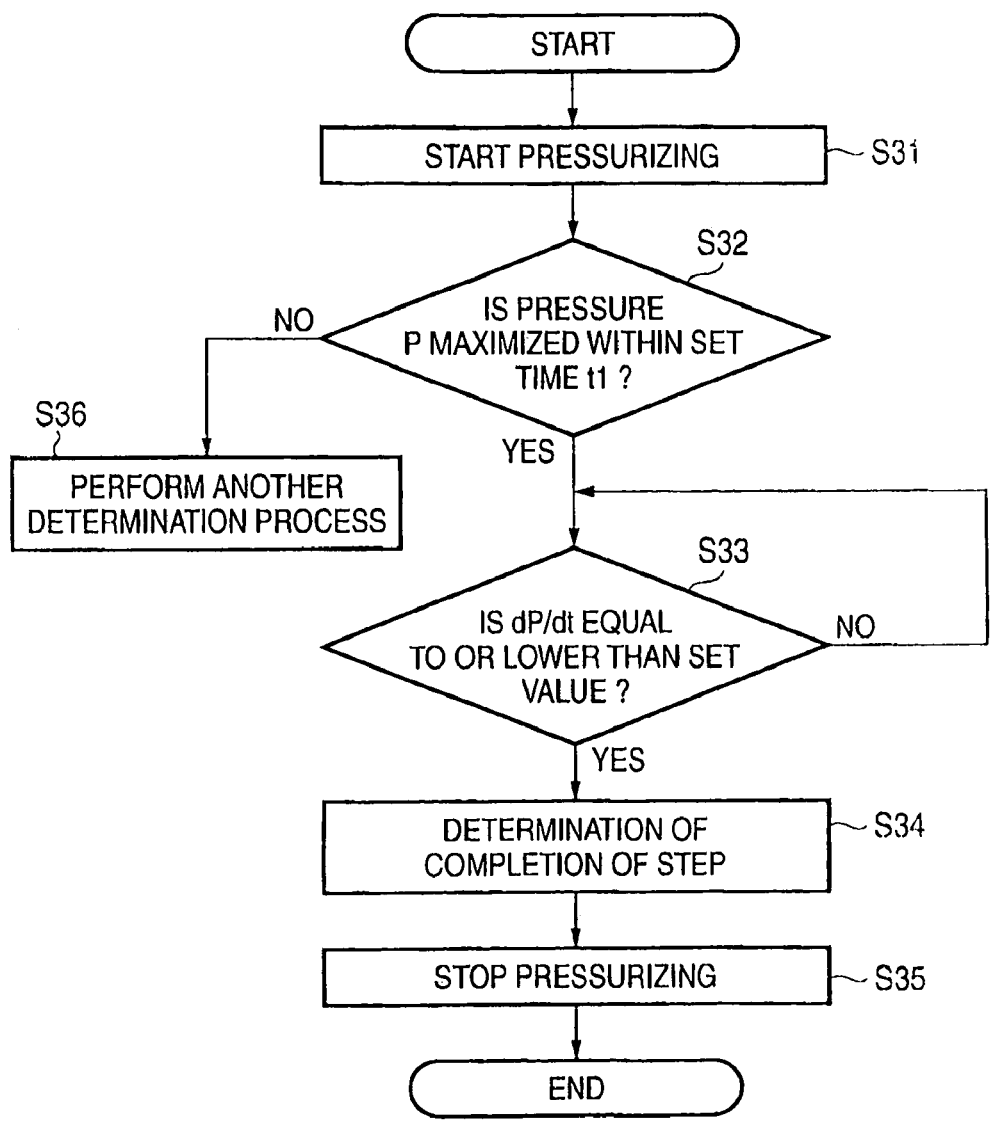

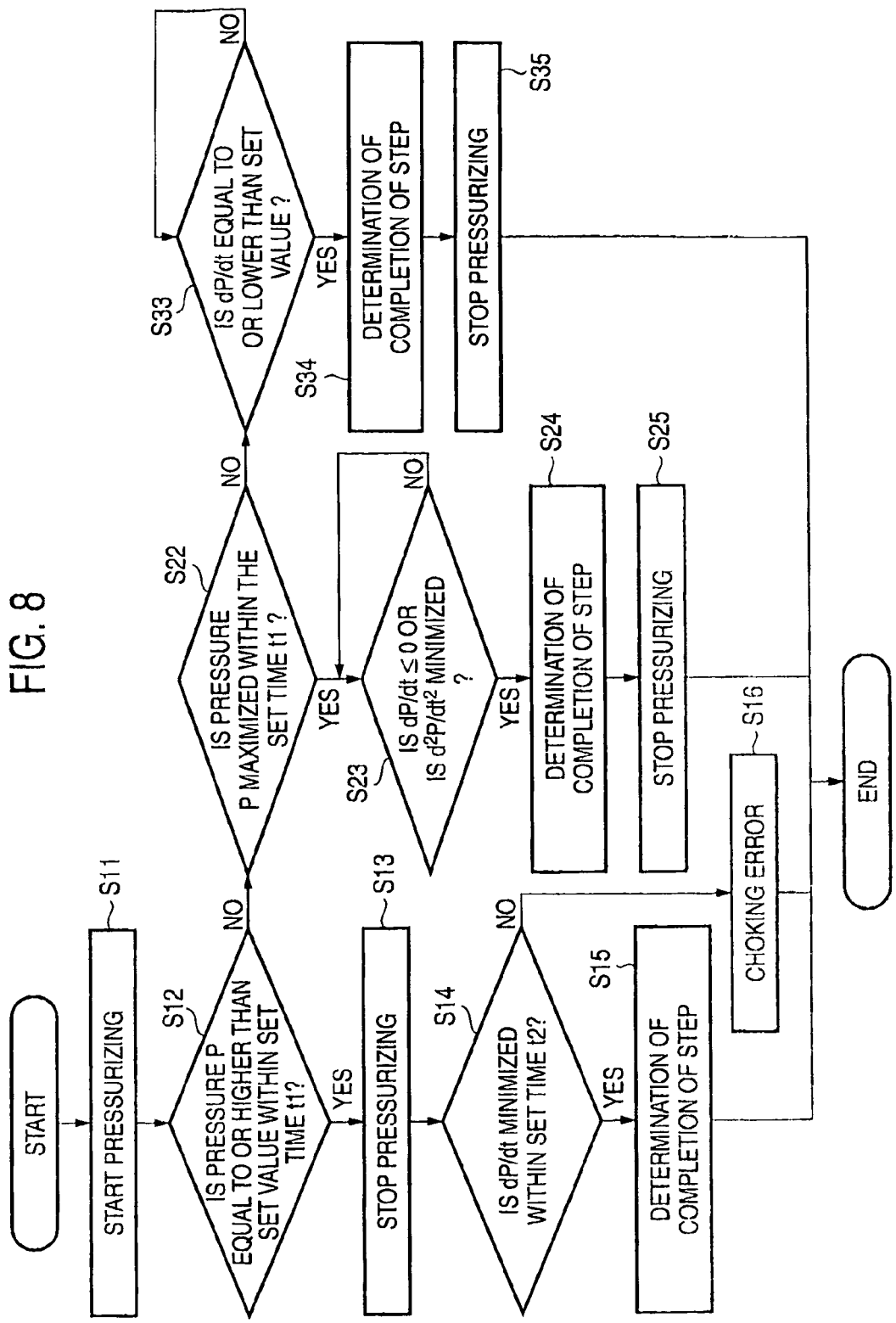

METHOD AND APPARATUS OF AUTOMATICALLY ISOLATING AND PURIFYING NUCLEIC ACID

TECHNICAL FIELD

The present invention relates to a method of automatically isolating and purifying nucleic acid and apparatus for automatically isolating and purifying nucleic acid. More particularly it relates to a technique for determining a completion of movement of a liquid in a process of moving the liquid by a pressure difference generated by a pressure generation means.

BACKGROUND ART

As a popularly known nucleic acid isolation and purification method, there is a method for adsorbing nucleic acid on a solid phase of silicon dioxide, silica polymer, magnesium silicate or the like and isolating and purifying nucleic acid by a succeeding operation of washing, desorption, and so on (e.g. Patent Document 1). This method is excellent in isolating performance but is insufficient in simplicity, rapidity, automation and miniaturization adaptability. There are problems in industrial difficulty in mass production of adsorbent media having the same performance, inconvenience in handling, difficulty in processing the adsorbent media to various shapes, and so on.

As a method for isolating and purifying nucleic acid easily and efficiently to solve the aforementioned problems, there has been disclosed a method in which a solution for adsorbing nucleic acid on a porous film and a solution for desorbing nucleic acid from the porous film are used, and nucleic acid is adsorbed/desorbed on/from a porous film made of an organic macromolecule having a hydroxyl group on its surface to thereby automatically isolate and purify nucleic acid on the oasis of pressurizing (Patent Document 2).

Concerning a pressurizing apparatus for supplying pressurized air to a isolator having a filter in its inside, there have been disclosed a pressurized air supply apparatus, a pressure sensor and an apparatus for stopping pressurizing when pressure detected by the pressure sensor becomes a set value or higher (Patent Document 3).

[Patent Document 1] Japanese Patent Publication No. 51065/1995

[Patent Document 2] Japanese Patent Laid-Open No. 2003-128691

[Patent Document 3] Japanese Patent Laid-Open No. 19883/1998

DISCLOSURE OF THE INVENTION

In Patent Document 1, there is however no description about a specific method for finding the timing of completion of each of the steps for purifying nucleic acid. In Patent Document 2, there is no description about algorithm for determining a point of time of completion of each step though the apparatus described in Patent Document 2 stops pressurizing and controls pressure to prevent hematolysis because hematolysis occurs when too high pressure is applied at the time of isolation of hematocytes. Moreover, even when this technique is used, it is practically impossible to determine a point of time of completion of each step before and after a point of set pressure because the time required for passage of the liquid and pressure and patterns of pressure change required for isolation vary according to the individual difference of the isolator having the filter in its inside, the kind of the filter, the individual difference due to the production lot of the filter, the difference in kind of the liquid to be used, and so on.

As described above, in the step of discharging the liquid injected into the container from the container by pressurizing, it is difficult to automatically determine the point of time of completion of discharge of the liquid accurately and rapidly because the time required for completion of discharge, and pressure and patterns of pressure change required for isolation vary according to the difference in kind of the nucleic acid-adsorbent solid phase stored in the container, the difference in production lot of the nucleic acid-adsorbent solid phase, the difference in production lot of the container per se, the difference in the container in each production lot, the kind of the liquid to be used, and so on.

The present invention is designed in consideration of the problems in the background art, and an object of the invention is to provide an method of automatically isolating and purifying nucleic acid and the apparatus, in which completion of discharge of a liquid can be automatically determined accurately and rapidly when the liquid is injected into the container having the nucleic acid-adsorbent solid phase stored therein and is discharged from the container through the nucleic acid-adsorbent solid phase on the basis of the pressure difference between the inside and outside of the container.

The present inventors have made eager examination to solve the aforementioned problems. As a result, it has been found that in the step of injecting a liquid into a container having a nucleic acid-adsorbent solid phase and two openings through one opening of the two openings and then pressurized and discharged from the container through the other opening, a completion of discharge of the liquid can be determined automatically by detecting patterns of temporal change of pressure parameters in a container in a combination by a pressure sensor in the middle of change of pressure. Thus, the invention is accomplished.

That is, the invention is configured as follows.

1. A method of automatically isolating and purifying nucleic acid from a nucleic acid-containing specimen, the method comprises:

injecting a liquid into a cartridge for isolation and purification of a nucleic acid including at least two openings from one opening of the at least two openings, in which the cartridge includes a container having the at least two openings and containing a nucleic acid-adsorbent solid phase;

passing the liquid through the nucleic acid-adsorbent solid phase by a pressure difference generated by a pressure generation means for generating a pressure difference between the inside and outside of the container; and discharging the liquid from the other opening of the container to the outside of the container by a pressure difference generated by the pressure generation means, wherein a pressure generated in the inside of the container by the pressure generation means is measured, a pressure change velocity and a pressure change acceleration are calculated on the basis of the value of the measured pressure, and the timing of completion of discharge of the liquid from the container is determined by use of a temporal change pattern of at least one of the measured pressure, the pressure change velocity and the pressure change acceleration.

2. The method according to the item 1, wherein, when the pressure of the inside of the container reaches a set value in the middle of pressurizing the inside of the cartridge by the pressure generation means, the pressurization by the pressure generation means is stopped, and a point of time when the pressure change acceleration in said container is minimized after the stop of pressurization is determined as the timing of completion of discharge of the liquid from the container.

3. The method according to the item 1 or 2, wherein, when the pressure of the inside of the container does not reach a set value in the middle of pressurizing the inside of the cartridge by the pressure generation means, at least one of a point of time when the pressure in the container is maximized and the pressure change velocity in the container becomes zero or less and a point of time when the pressure in the container is maximized and the pressure change acceleration in the container is minimized, is determined as the timing of completion of discharge of the liquid from the container.

4. The method according to any one of the items 1 to 3, wherein, when the pressure of the inside of the container does not reach a set value and is not maximized in the middle of pressurizing the inside of the cartridge by the pressure generation means, a point of time when the pressure change velocity in the container becomes lower than a threshold value, is determined as the timing of completion of discharge of the liquid from the container.

5. The method according to any one of the items 1 to 4, which comprises:

(1) injecting and pressurizing a nucleic acid-containing specimen liquid into the container through one of the at least two openings, and discharging the nucleic acid-containing specimen liquid from the other opening to thereby adsorb a nucleic acid contained in the nucleic acid-containing specimen liquid to the nucleic acid-adsorbent solid phase;

(2) dispensing and pressurizing a washing liquid into the container through one of the at least two openings, and discharging the washing liquid from the container through the other opening to remove impurities; and (3) dispensing and pressurizing an elution liquid into the container through one of the at least two openings to isolate and discharge the nucleic acid adsorbed to the nucleic acid-adsorbent solid phase from the container through the other opening together with the elution liquid to thereby collect nucleic acid.

6. The method according to the item 5, wherein in response of the determined timing of completion of discharge of the liquid, the subsequent step is performed.

7. An automatic nucleic acid isolation and purification apparatus for isolating and purifying nucleic acid from a nucleic acid-containing specimen, the apparatus comprising:

a cartridge for isolation and purification of a nucleic acid, in which the cartridge includes a container having at least two openings and containing a nucleic acid-adsorbent solid phase;

a pressure generation means for generating a pressure difference between the inside and outside of the container in the cartridge, in which a liquid injected into the container through one of the at least two openings is discharged from the other opening to the outside of the container through the nucleic acid-adsorbent solid phase by a pressure difference generated by the pressure generation means; and a control portion for discharging the liquid from the container on the basis of the method according to any one of the items 1 to 6.

8. The apparatus according to the item 7, which further comprises a means for measuring a pressure of the inside of the container.

9. The apparatus according to the item 8, wherein the control portion comprises: an arithmetic means for calculating at least one of a pressure change velocity and pressure change acceleration on the basis of the value of the measured pressure; and a determination means for determining the timing of the completion of discharge of the liquid on the basis of the information from the arithmetic means, in which, in response of the determined timing of completion of discharge of the liquid, the subsequent step is performed.

10. The apparatus according to any one of the items 7 to 9, wherein the nucleic acid-adsorbent solid phase is a porous material including an organic macromolecule capable of absorbing a nucleic acid by a weak interaction not concerned with an ionic bond.

11. The apparatus according to the item 10, wherein the porous material includes an organic macromolecule having a hydroxyl group.

12. The apparatus according to any one of the items 7 to 11, wherein the nucleic acid-adsorbent solid phase includes an organic material prepared by saponifying a mixture of acetyl celluloses different in an acetyl value.

13. The apparatus according to the item 12, wherein the saponification rate of said mixture is not lower than 5%.

14. The apparatus according to the item 12 or 13, wherein the organic material is a saponified mixture of triacetyl cellulose and diacetyl cellulose.

15. The apparatus according to any one of the items 7 to 14, wherein the nucleic acid-adsorbent solid phase is a porous film, of which the front and back sides are asymmetrical with each other.

BRIEF DESCRIPTION OF THE DRAWINGS

FIGS. 2A to 2C show a profile in a first pattern in the case where pressure reaches a set value within a set time, FIG. 2A being a graph showing temporal change of pressure, FIG. 2B being a graph showing temporal change of pressure change velocity, FIG. 2C being a graph showing temporal change of pressure change acceleration.

FIG. 3 is a flow chart showing a procedure of determining completion of the step in the case where the first pattern is exhibited.

FIG. 5 is a flow chart showing a procedure of determining completion of the step in the case where the second pattern is exhibited.

FIG. 7 is a flow chart showing a procedure of determining completion of the step in the case where the third pattern is exhibited.

FIG. 8 is a flow chart showing combination of determination algorithms shown in FIGS. 3, 5 and 7.

Figure 1:
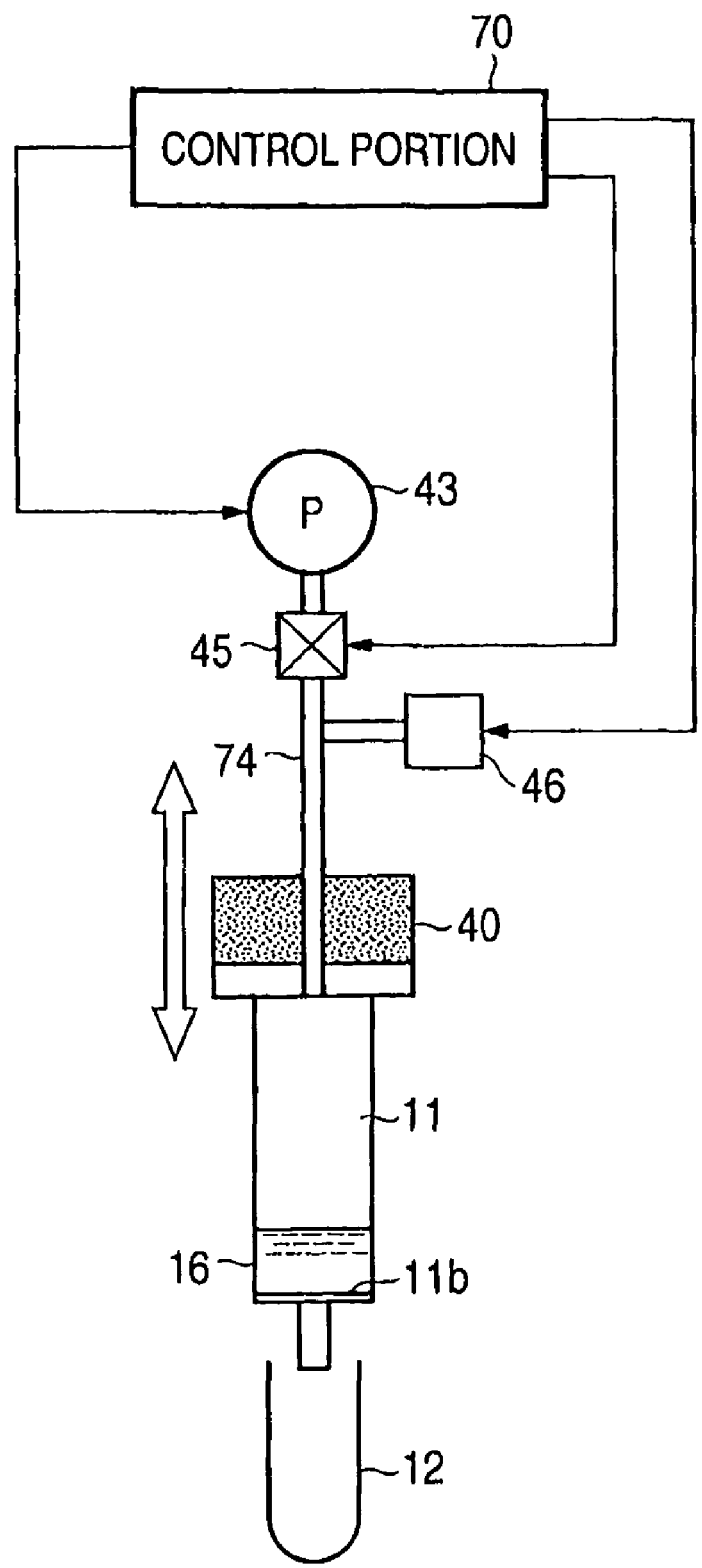
FIG. 1 is a schematic block diagram showing the configuration of important part for automatically determining completion of a liquid discharge step in a nucleic acid isolation and purification process according to the invention.

DESCRIPTION OF THE REFERENCE NUMERALS AND SYMBOLS 1 nucleic acid extraction apparatus (nucleic acid isolation and purification apparatus)
2 apparatus body
3 mount mechanism
4 pressurized air supply mechanism
5 dispensing mechanism
6 rack
11 cartridge for isolation and purification of nucleic acid
11b nucleic acid-adsorbent porous film
11c discharge portion (other opening)
11e upper opening (one opening)
12 waste container
13 collection container
16 liquid
14 suction flow passage
18 air
40 pressurizing head
41 air nozzle
43 air pump (pressure generation device)
45 on-off valve
46 pressure sensor
51w, 51r dispensing nozzle
52w, 52r supply pump
56w, 56r bottle
70 control portion
S specimen liquid
W washing liquid
R elution liquid

BEST MODE FOR CARRYING OUT THE INVENTION

A preferred embodiment of the invention as to an method of automatically isolating and purifying nucleic acid and the apparatus will be described below in detail with reference to the drawings.

FIG. 1 is a schematic block diagram showing the configuration of important part for automatically determining the termination of a liquid discharge step in a nucleic acid isolation and purification process according to the invention.

This apparatus includes cartridge for isolation and purification of a nucleic acid (hereinafter simply referred to as "cartridge") 11 containing a porous filter 11b as a nucleic acid-adsorbent solid phase in its inside, and a pressurizing head 40 detachably attached to the cartridge 11 so that the pressurizing head 40 can be moved up and down by control according to detection by a position sensor not shown. The pressurizing head 40 is connected to a pump 43 through an electromagnetic valve 45 which serves as an on-off valve. A pressure sensor 46 is interposed in the middle of a connected piping 74 so that pressure in the piping 74 is measured. Measurement results of the position sensor and the pressure sensor 46 are input to a control portion 70. The pressure, pressure change velocity and pressure change acceleration as well as positional information of a pressurizing nozzle are calculated by the control portion 70, so that the operations of the pump 43, the electromagnetic valve 45 and the pressurizing head 40 are controlled by predetermined programmed algorithm for automatically determining the termination of a discharge step. That is, the control portion 70 serves as arithmetic means for calculating the pressure change velocity and pressure change acceleration and also as determination means for determining the timing of the termination of liquid discharge on the basis of the information.

A pressure signal given to the control portion 7 is sampled at intervals of a predetermined time and usually calculated as an average value per second in order to avoid misdetermination of the algorithm because of noise. It is preferable that the predetermined time interval is not larger than 0.5 sec. The pressure change velocity $dP/dt$ obtained by differentiating pressure with respect to time and the pressure change acceleration $d^2P/dt^2$ obtained by differentiating the pressure change velocity with respect to time are usually calculated as average values per second and used for the determination of the algorithm.

Next, the algorithm for automatically determining the termination of the liquid discharge step will be described on the basis of temporal change in pressure, pressure change velocity and pressure change acceleration in the cartridge 11 at the time of discharge of a liquid 16 injected into the cartridge 11 containing the nucleic acid-adsorbent solid phase.

The temporal change in pressure, pressure change velocity and pressure change acceleration varies widely according to the kind of the nucleic acid-adsorbent solid phase contained in the cartridge 11 and the kind of a specimen. Accordingly, the temporal change is classified into three typical patterns.

(First Pattern)

FIGS. 2A to 2C are graphs showing temporal change in pressure, pressure change velocity and pressure change acceleration respectively in a first pattern. FIGS. 2A to 2C show a profile in the case where the pressure reaches a set value within a set time. FIG. 3 is a flow chart showing a procedure of process termination determination in the case where temporal change exhibits the first pattern.

First, after a specimen containing nucleic acid is injected into the cartridge 11, the pressurizing head 40 is attached to the cartridge 11. Then, pressurizing the inside of the cartridge 11 by the pump 43 starts (step 11, hereinafter abbreviated to S11). Incidentally, the pressure is set by adjustment of the electromagnetic valve 45 and measured by the pressure sensor 46. After pressurizing starts, the pressure of the inside of the cartridge 11 increases. When the pressure reaches a predetermined set value $P_1$ within a predetermined set time $t_1$ (S12), pressurizing by means of the pump 43 is stopped (S13). As a result, the specimen in the cartridge 11 passes through the filter 11b as a nucleic acid-adsorbent solid phase on the basis of the pressure, so that the specimen is discharged from the cartridge 11. As the amount of the specimen in the cartridge 11 decreases, the pressure P of the inside of the cartridge 11 decreases from $P_a$ to $P_b$.

When pressurized air is extruded out of the cartridge 11 after all the specimen is discharged from the cartridge 11, the pressure P of the inside of the cartridge 11 decreases rapidly. On this occasion, pressure acceleration $d^2P/d^2$ reaches a minimum $a_1$. For this reason, when the point of time that pressure acceleration $d^2P/dt^2$ reaches the minimum is detected (S14) after the pump is stopped, a decision is made that discharge is terminated, that is, the process is terminated (S15). When pressure acceleration $d^2P/dt^2$ does not reach the minimum within a set time $t_2$, a decision is made that choking error occurs (S16). In this case, controlling is performed to operate the electromagnetic valve 45 to open the pressure of the inside of the cartridge 11 to the atmospheric air. The set times $t_1$ and $t_2$ and the set pressure $P_1$ can be decided at option.

Although the pressure of the inside of the cartridge 11 increases after pressurizing starts, another determination step may be carried out (S17) when the pressure does not reach the set value $P_1$ within the predetermined set time $t_1$.

(Second Pattern)

Figure 4A:
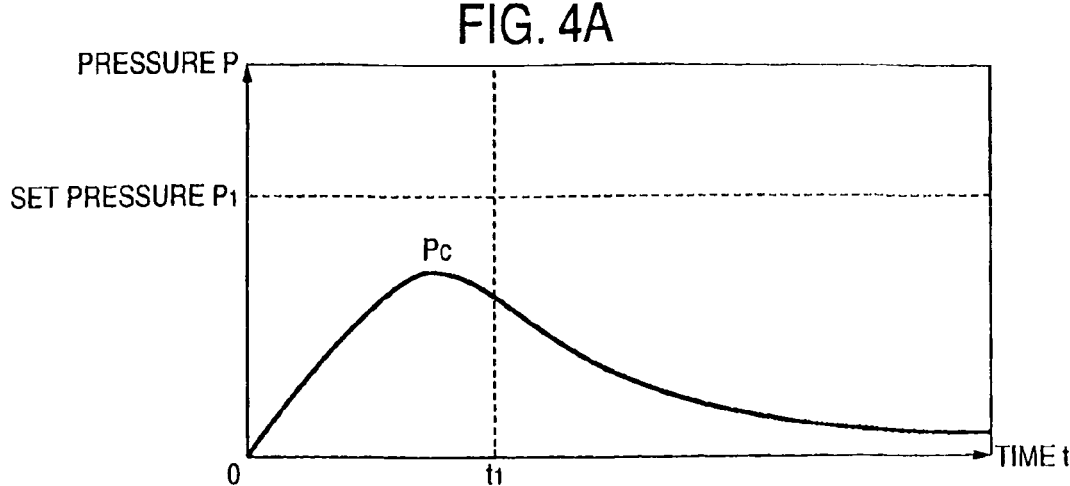
FIGS. 4A to 4C show a profile in a second pattern in the case where pressure P does not reach a set value $P_1$ within a set time $t_1$ but maximized within the set time $t_1$, FIG. 4A being a graph showing temporal change of pressure, FIG. 4B being a graph showing temporal change of pressure change velocity, FIG. 4C being a graph showing temporal change of pressure change acceleration.
Figure 4B:
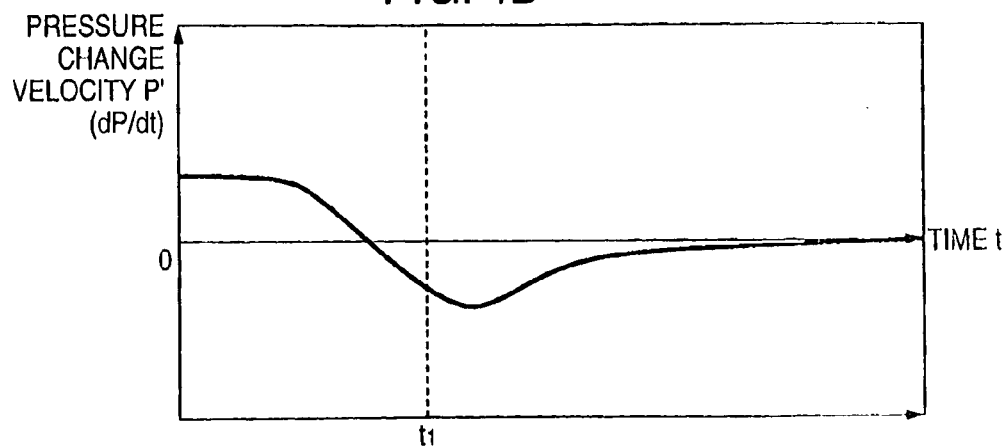
Figure 4C:
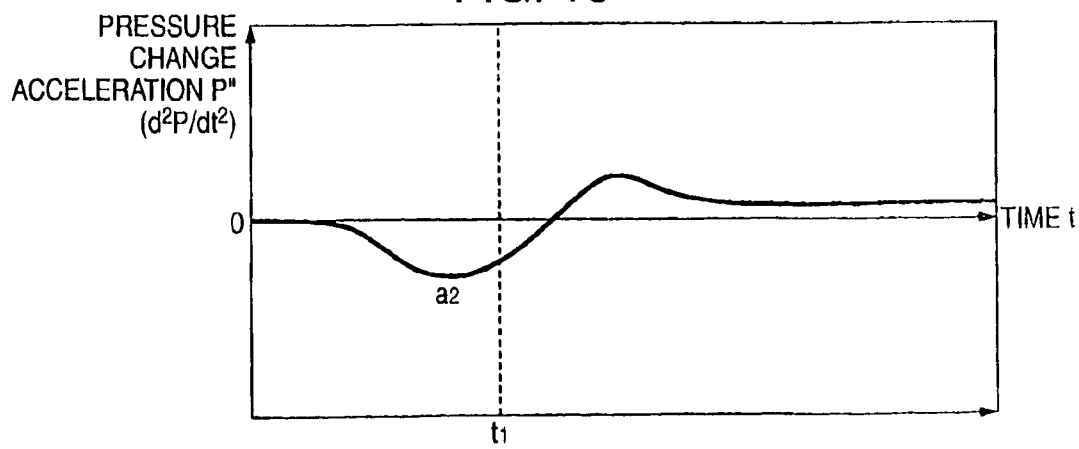

FIGS. 4A to 4C are graphs showing temporal change in pressure, pressure change velocity and pressure change acceleration respectively in a second pattern. FIGS. 4A to 4C show a profile in the case where the pressure P does not reach the set value $P_1$ within the set time $t_1$ but reaches a maximum within the set time $t_1$. FIG. 5 is a flow chart showing a procedure of process termination determination in the case where temporal change exhibits the second pattern.

As described above in the first pattern, first, after a specimen containing nucleic acid is injected into the cartridge, the pressurizing head 40 is attached to the cartridge 11. When pressurizing by means of the pump 43 then starts (S21), the specimen in the cartridge 11 passes through the filter 11b as a nucleic acid-adsorbent solid phase and is discharged out of the cartridge 11. As a result, the pressure of the inside of the cartridge 11 increases. With the passage of time, the pressure change velocity decreases and the pressure P reaches a maximum $P_C$. On this occasion, the pressure velocity becomes zero and the pressure acceleration reaches a minimum $a_2$. For this reason, the condition that the pressure P reaches a maximum within the set time $t_1$ (S22) while the pressure velocity is not higher than zero or while the pressure acceleration reaches a minimum is determined (S23). At the point of time that this condition is satisfied, a decision is made that discharge is terminated, that is, the process is terminated (S24). Therefore, the pump 43 is stopped (S25). Incidentally, the timing of stopping the pump 43 can be decided at option if the timing is after the point of time that a decision is made that discharge is terminated.

Although the pressure of the inside of the cartridge 11 increases after pressurizing starts, another determination step may be carried out (S26) when the pressure P does not reach the maximum within the set time $t_1$.

(Third Pattern)

Figure 6A:
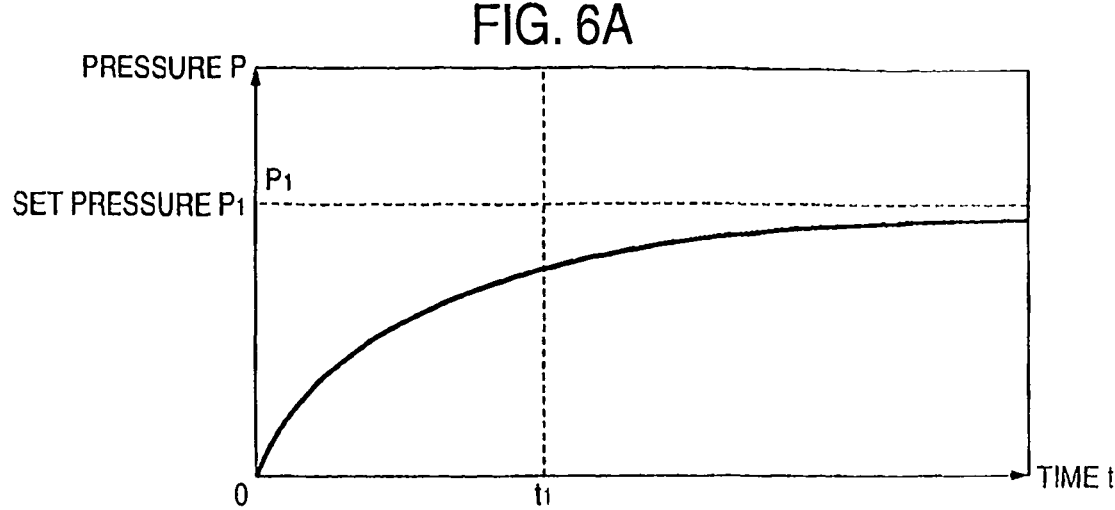
FIGS. 6A to 6C show a profile in a third pattern in the case where pressure P does not reach a set value $P_1$ within a set time $t_1$ and is not maximized within the set time $t_1$, FIG. 6A being a graph showing temporal change of pressure, FIG. 6B being a graph showing temporal change of pressure change velocity, FIG. 6C being a graph showing temporal change of pressure change acceleration.
Figure 6B:
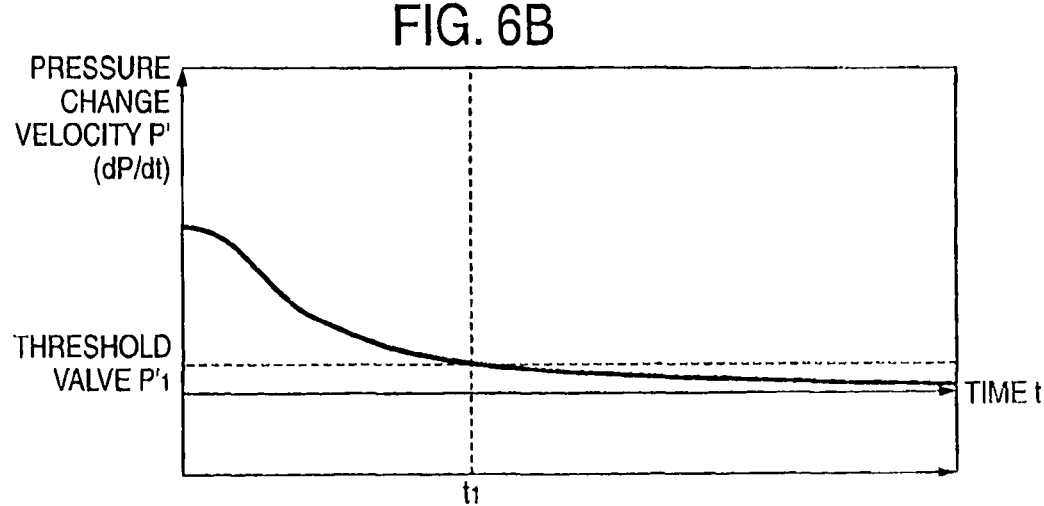
Figure 6C:
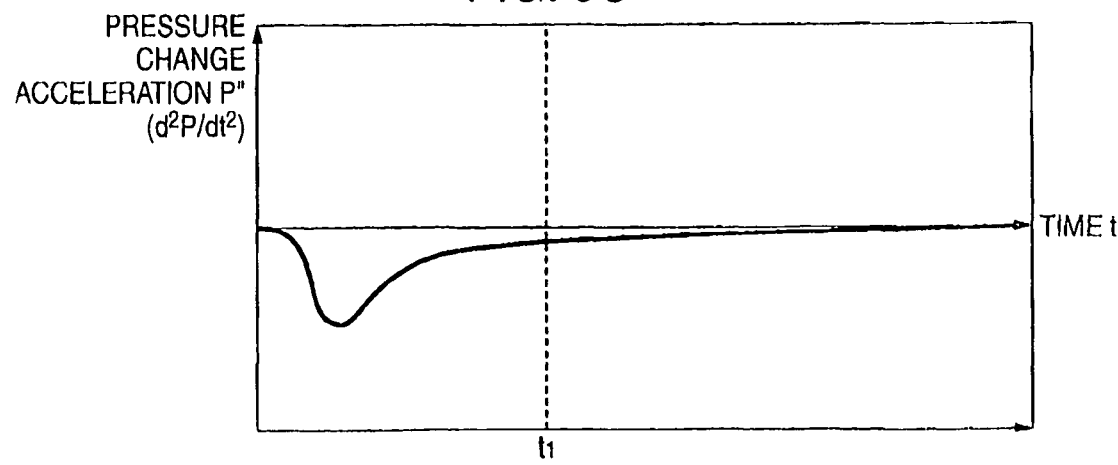

FIGS. 6A to 6C are graphs showing temporal change in pressure, pressure change velocity and pressure change acceleration respectively in a third pattern. FIGS. 6A to 6C show a profile in the case where the pressure P neither reaches the set value $P_1$ within the set time $t_1$ nor reaches a maximum within the set time $t_1$. FIG. 7 is a flowchart showing a procedure of process termination determination in the case where temporal change exhibits the third pattern.

As described above in the first and second patterns, first, after a specimen containing nucleic acid is injected into the cartridge, the pressurizing head 40 is attached to the cartridge 11. When pressurizing by means of the pump 43 then starts (S31), the specimen in the cartridge passes through the nucleic acid-adsorbent solid phase and is discharged out of the cartridge 11. As a result, the pressure of the inside of the cartridge 11 increases. In this case, however, the pressure change velocity decreases slowly with the passage of time. In this manner, when the pressure does not have any maximum within the set time $t_1$ (S32), a decision is made that discharge is terminated, that is, the process is terminated (S34) at the time that the pressure change velocity reaches a set threshold $P'_1$ or lower (S33). As a result, the pump 43 is stopped (S35). Incidentally, the timing of stopping the pump can be decided at option if the timing is after the point of time that a decision is made that discharge is terminated. The predetermined threshold $P'_1$ of the pressure change velocity can be set at any value.

As described above, in order to automatically determine the termination of the process in which a liquid is injected into the cartridge containing the filter 11b as a nucleic acid-adsorbent solid phase and pressurized so as to be discharged, it is preferable that a program is provided so that an optimum determination algorithm is selected from three determination algorithms while a determination is made as to which of the three patterns is valid. An example of the automatic determination will be described below.

(Automatic Determination of all Patterns)

FIG. 8 is a flow chart combined with the determination algorithms shown in FIGS. 3, 5 and 7.

First, a determination is made as to whether the pressure P reaches a set value $P_1$ or higher within a set time $t_1$ after start of pressurizing. When the pressure P is not lower than the set value $P_1$, the termination of the process is determined in accordance with the above description with reference to FIGS. 2A to 2C and FIG. 3. When the pressure P is lower than the set value $P_1$, a determination is made as to whether the pressure P reaches a maximum within the set time $t_1$. When the pressure P reaches the maximum, the termination of the process is determined in accordance with the above description with reference to FIGS. 4A to 4C and FIG. 5. When the pressure P does not reach any maximum within the set time $t_1$, the termination of the process is determined in accordance with the above description with reference to FIGS. 6A to 6C and FIG. 7.

According to this configuration, the termination of the process can be determined appropriately for any one of the first, second and third patterns, so that the termination of the process can be determined accurately by use of an optimum algorithm in accordance with the fit pattern. As a result, discharge of the liquid can be completed in the required minimum time without continuing wasteful pressurizing in the process, so that reduction in tact time can be attained.

As described above, the first, second and third typical patterns have been illustrated and the determination algorithms for determining these patterns have been described. Even if any other pattern than these patterns is generated, the determination algorithms can be combined suitably to determine the termination of the process accurately and rapidly in the same manner as described above.

Next, an example in which the aforementioned determination of the termination of the liquid discharge step is applied to a nucleic acid isolation and purification method will be described.

First, the nucleic acid isolation and purification method at least includes the steps of: (1) passing a nucleic acid-containing specimen liquid through a nucleic acid-adsorbent porous material (nucleic acid-adsorbent porous film) to adsorb nucleic acid into the porous film; (2) washing the nucleic acid-adsorbent porous film in a state in which the nucleic acid is adsorbed onto the nucleic acid-adsorbent porous film; and (3) passing an elution liquid through the nucleic acid-adsorbent porous film to desorb the nucleic acid from the inside of the porous film.

Preferably, in each of the steps (1), (2) and (3), the nucleic acid-containing specimen liquid, a washing liquid, a DNase solution or the collection solution is made to pass through the nucleic acid-adsorbent porous film while pressurized. More preferably, in each of the steps (1), (2) and (3), the nucleic acid-containing specimen liquid, the washing liquid or the elution liquid is injected into one opening of the cartridge 11 including the nucleic acid-adsorbent porous film stored in a container having at least two openings, and the injected solution or liquid is made to pass through the porous film so as to be discharged from the other opening while the inside of the cartridge 11 is pressurized by a pressure difference generator connected to one opening of the cartridge 11. When the nucleic acid-containing specimen liquid, the washing liquid or the elution liquid is made to pass through the porous film while pressurized, the apparatus can be preferably automated compactly. Pressurizing is made preferably in a range of from 10 to 200 kPa, more preferably in a range of from 40 to 100 kPa.

In the nucleic acid isolation and purification process, all the procedure of from the first step of injecting the nucleic acid-containing specimen liquid to the step of obtaining nucleic acid in the outside of the cartridge can be completed within 10 minutes, especially within 2 minutes in a preferred condition. The nucleic acid isolation and purification process can yield 50 mass % or more of nucleic acid, especially 90 mass % or more of nucleic acid in a preferred condition, with respect to the total amount of nucleic acid contained in the specimen.

Examples of the pressure difference generator used in the aforementioned process include: an inflatable pump such as an injector, a pipetter or a peristaltic pump; and a deflatable material such as an evaporator. Among these, the injector is suitable for manual operation and the pump is suitable for automatic operation. The pipetter has an advantage that it can be operated easily by a single hand. Preferably, the pressure difference generator is detachably attached to one opening of the cartridge.

The specimen allowed to be used in this invention is not limited but, for example, humors such as whole blood, blood plasma, blood serum, urina, feces, semen or saliva taken as a specimen or solutions prepared from biological materials such as a plant (or part thereof), an animal (or part thereof), bacteria, virus or a dissolution or homogenate thereof are used in the diagnostic field.

First, these specimens are treated with an aqueous solution containing a reagent (nucleic acid solubilizing reagent) for dissolving cell membranes and nuclear membranes to thereby solubilize nucleic acid. As a result, cell membranes and nuclear membranes are dissolved and the nucleic acid is dispersed into the aqueous solution, so that a nucleic acid-containing specimen liquid is prepared.

A process of dissolving cell membranes to solubilize nucleic acid to prepare a nucleic acid-containing specimen liquid from a specimen will be described below. In the invention, a nucleic acid solubilizing reagent is used for dissolving cell membranes to solubilize nucleic acid. An example of the nucleic acid solubilizing reagent is a solution containing chaotropic salt, and a surfactant.

An example of the method for dissolving cell membranes to solubilize nucleic acid to prepare a nucleic acid-containing specimen liquid from a specimen can be a method including the steps of: (I) injecting a cell-containing or virus-containing specimen into a container; (II) adding a nucleic acid solubilizing reagent solution containing chaotropic salt and a surfactant into the container to mix the nucleic acid solubilizing reagent solution with the specimen; and (III) adding a water-soluble organic solvent into the mixture solution obtained by the aforementioned step.

In the process for dissolving cell membranes to solubilize nucleic acid to prepare a nucleic acid-containing specimen liquid from a specimen, optimization of automation is improved when the specimen is homogenized. Homogenization can be made by a treatment such as an ultrasonic treatment, a treatment using a high-speed agitating treatment using a sharp-edged protrusion from fine voids or a treatment using glass beads.

The method for mixing the nucleic acid solubilizing reagent solution containing chaotropic salt and a surfactant with the specimen is not particularly limited.

It is preferable that the two are mixed with each other for a time of from 1 second to 3 minutes by an agitator rotating at a speed of from 30 to 3000 rpm. In this manner, the yield of nucleic acid isolated and purified can be increased. Or it is preferable that the two are mixed with each other by repeating reversing mixture by 5 times to 30 times. Or the two may be mixed with each other by repeating pipetting by 10 tines to 50 times. In this case, the yield of nucleic acid isolated and purified can be increased by a simple operation.

The nucleic acid-adsorbent porous film used in the invention and the adsorbing process will be described below. The nucleic acid-adsorbent porous film used in the invention can transmit the solution through its inside. The phrase "can transmit the solution through its inside" means that the solution can be transmitted from a high-pressure space side to a low-pressure space side through the inside of the film when a pressure difference is generated between a space adjacent to one surface of the film and a space adjacent to the other surface of the film. Or the phrase means that the solution can be transmitted in a centrifugal direction through the inside of the film when centrifugal force is applied to the film.

The nucleic acid-adsorbent porous film used in the invention is characterized to be a porous film onto which nucleic acid is adsorbed by an interaction substantially irrespective of any ionic bond. What is meant by this is that the porous film is not ionized as the porous film side condition in use. It is supposed that the nucleic acid and the porous film will attract each other when environmental polarity is changed. As a result, nucleic acid can be isolated and purified while both isolating performance and washing efficiency can be kept excellent. Preferably, the nucleic acid-adsorbent porous film is a porous film having a hydrophilic group. It is supposed that hydrophilic groups of the nucleic acid and the porous film will attract each other when environmental polarity is changed. The term "porous film having a hydrophilic group" means a porous film made of a material having a hydrophilic group or a porous film made of a material into which a hydrophilic group is introduced by treatment or coating. The material forming the porous film may be an organic material or an inorganic material. Examples of the porous film include: a porous film made of an organic material having a hydrophilic group; a porous film made of an organic material having no hydrophilic group but treated so that a hydrophilic group is introduced into the porous film; a porous film made of an organic material having no hydrophilic group out coated with a material having a hydrophilic group so that the hydrophilic group is introduced into the porous film; a porous film made of an inorganic material having a hydrophilic group; a porous film made of an inorganic material having no hydrophilic group but treated so that a hydrophilic group is introduced into the porous film; and a porous film made of an inorganic material having no hydrophilic group but coated with a material having a hydrophilic group so that the hydrophilic group is introduced into the porous film. From the point of view of processability, an organic material such as an organic macromolecule is preferably used as the material for forming the porous film.

The term "hydrophilic group" means a polar group (atomic group) which can interact with water. All groups (atomic groups) concerning adsorption of nucleic acid are equivalent to the hydrophilic groups. A group which can interact with water at a medium strength (see "medium hydrophilic group" written in the item "hydrophilic group" in Chemical Dictionary published by Kyoritsu Shuppan Co., Ltd.) is preferred as the hydrophilic group. Examples of the hydrophilic group include hydroxyl group, carboxyl group, cyano group, oxyethylene group, etc. Especially, hydroxyl group is preferred.

An example of the porous film having a hydrophilic group is a porous film made of an organic material having a hydroxyl group. An example of the organic material having a hydroxyl group is a surface saponified of acetyl cellulose described in Japanese Patent Laid-Open No. 2003-128691. Acetylcellulose can be selected from monoacetyl cellulose, diacetyl cellulose and triacetyl cellulose. Especially, triacetyl cellulose is preferred. In this case, the amount (density) of the hydroxyl group in a solid phase surface can be controlled by the degree of saponification (saponification rate). To improve the nucleic acid isolating efficiency, it is preferable that the amount (density) of the hydroxyl group is high. For example, in the case of acetyl cellulose such as triacetyl cellulose, the saponification rate (surface saponification rate) is selected to be preferably in a range of from about 5 to 100%, more preferably in a range of from 10 to 100%. To increase the surface area of the organic macromolecule having a hydroxyl group, it is preferable that the porous film of acetyl cellulose is saponified. In this case, a porous film of which the front and back sides are symmetrical with each other may be used as the porous film or a porous film of which the front and back sides are asymmetrical with each other may be preferably used as the porous film.

The term "saponification" means a treatment for bringing acetyl cellulose into contact with a saponification solution (such as an aqueous solution of sodium hydroxide). By this treatment, part of the acetyl cellulose in contact with the saponification solution is changed to regenerated cellulose so that the hydroxyl group can be introduced into the porous film.

To change the saponification rate, the sodium hydroxide concentration used in the saponification may be changed. The saponification rate can be measured easily by an NMR, an IR or an XPS. (For example, the saponification rate can be decided on the basis of the degree of reduction in peaks of carbonyl groups).

Examples of the porous film made of an organic material having a hydroxyl group include porous films made of polyhydroxyethyl acrylate, polyhydroxyethyl methacrylate, polyvinyl alcohol, polyvinyl pyrrolidone, polyacrylate, polymethacrylate, polyoxyethylene, acetyl cellulose, mixture of acetyl celluloses different in acetyl number, etc. Especially, a porous film made of an organic material having a polysaccharide structure can be preferably used.

Particularly a porous film of an organic macromolecule including a mixture of acetyl celluloses different in acetyl value can be preferably used as the porous film of an organic material having a hydroxyl group. Preferable examples of the mixture of acetyl celluloses different in acetyl number include: a mixture of triacetyl cellulose and diacetyl cellulose; a mixture of triacetyl cellulose and monoacetyl cellulose; a mixture of triacetyl cellulose, diacetyl cellulose and monoacetyl cellulose; and a mixture of diacetyl cellulose and monoacetyl cellulose.

Especially, a mixture of triacetyl cellulose and diacetyl cellulose can be preferably used. The mixture rate (mass rate) of triaceyl cellulose to diacetyl cellulose is preferably in a range of from 99:1 to 50:50.

A porous film made of an organic material prepared by saponifying a mixture of acetyl celluloses different in acetyl number can be preferably used as the porous film of an organic material having a hydroxyl group. Preferable examples of the organic material prepared by saponifying a mixture of acetyl celluloses different in acetyl number include: a saponified mixture of triacetyl cellulose and diacetyl cellulose; a saponified mixture of triacetyl cellulose and monoacetyl cellulose; a saponified mixture of triacetyl cellulose, diacetyl cellulose and monoacetyl cellulose; and a saponified mixture of diacetyl cellulose and monoacetyl cellulose. Especially, a saponified mixture of triacetyl cellulose and diacetyl cellulose can be preferably used.

The mixture ratio (mass ratio) of triacetyl cellulose to diacetyl cellulose is preferably selected to be in a range of from 99:1 to 50:50.

A porous film of cellulose can be preferably used as the porous film of an organic material having a hydroxyl group. A porous film of regenerated cellulose can be preferably used as the porous film of cellulose. Regenerated cellulose is prepared by saponifying a solid surface or whole of acetyl cellulose. Regenerated cellulose is different from original cellulose in crystalline state or the like.

As a method for introducing a hydrophilic group into the porous film of an organic material having no hydrophilic group, a graft polymer chain having a hydrophilic group in a polymer chain or in a side chain can be bonded to the porous film.

Two methods may be used as the method for bonding the graft polymer chain to the porous film of an organic material. That is, there are a method for chemically bonding the porous film and the graft polymer chain to each other and a method for polymerizing a compound having polymerizable double bonds with the porous film as a start point to thereby form a graft polymer chain.

First, in the method for attaching the porous film and the graft polymer chain to each other by chemical bonding, a polymer having a functional group capable of reacting with the porous film in a terminal or side chain of the polymer is used so that this functional group chemically reacts with a functional group of the porous film so as to be grafted to the functional group of the porous film. The functional group capable of reacting with the porous film is not particularly limited if it can react with the functional group of the porous film. Examples of the functional group include: a silane coupling group such as alkoxysilane; an isocyanate group; an amino group; a hydroxyl group; a carboxyl group; a sulfonic group; a phosphoric group; an epoxy group; an allyl group; a methacryloyl group; and an acryloyl group.

Examples of a compound especially useful as the polymer having a reactive functional group on a terminal or side chain of the polymer include: a polymer having a trialkoxysilyl group in a terminal of the polymer; a polymer having an amino group in a terminal of the polymer; a polymer having a carboxyl group in a terminal of the polymer; a polymer having an epoxy group in a terminal of the polymer; and a polymer having an isocyanate group in a terminal of the polymer. The polymer used in this case is not particularly limited if it has a hydrophilic group concerning adsorption of nucleic acid. Specific examples of the polymer include: polyhydroxyethyl acrylate, polyhydroxyethyl methacrylate and salt thereof; polyvinyl alcohol, polyvinyl pyrrolidone, polyacrylate, polymethacrylate and salt thereof; and polyoxyethylene.

The method for polymerizing a compound having polymerizable double bonds with the porous film as a start point to thereby form a graft polymer chain is generally called "surface graft polymerization". The surface graft polymerization method is a method in which an active seed is given onto a substrate surface by means of plasma irradiation, light irradiation, heating or the like so that a compound having polymerizable double bonds and disposed so as to be adjacent to the porous film is bonded to the porous film by polymerization. The compound useful for forming the graft polymer chain bonded to the substrate needs to have two characteristics, that: is, the compound needs to have polymerizable double bonds and also has a hydrophilic group concerning adsorption of nucleic acid. Any compound such as a polymer, an oligomer or a monomer having a hydrophilic group can be used as the compound if the compound has a double bond in a molecule. A monomer having a hydrophilic group is an especially useful compound.

Specific examples of the especially useful monomer having a hydrophilic group are as follows. For example, hydroxyl group-containing monomers such as 2-hydroxyethyl acrylate, 2-hydroxyethyl methacrylate, glycerol monomethacrylate, etc. can be especially preferably used. Carboxyl group-containing monomers such as acrylic acid, methacrylic acid, etc. or alkali-metal salt and amine salt thereof can be preferably used.

As another method for introducing a hydrophilic group into the porous film of an organic material having no hydrophilic group, the porous film may be coated with a material having a hydrophilic group. The material used for coating is not particularly limited if it has a hydrophilic group concerning adsorption of nucleic acid. From the point of view of easiness of operation, a polymer of an organic material is preferred. Examples of the polymer may include: polyhydroxyethyl acrylate, polyhydroxyethyl methacrylate, and salt thereof; polyvinyl alcohol, polyvinyl pyrrolidone, polyacrylate, polymethacrylate, and salt thereof; and polyoxyethylene, acetyl cellulose, and a mixture of acetyl celluloses different in acetyl number. Especially, a polymer having a polysaccharide structure is preferred.

After the porous film of an organic material having no hydrophilic group is coated with acetyl cellulose or a mixture of acetyl celluloses different in acetyl value, the acetyl cellulose or the mixture of acetyl celluloses different in acetyl value for use in coating may be saponified. In this case, the saponification rate is preferably selected to be not lower than about 5%. Especially, the saponification rate is preferably selected to be not lower than about 10%.

An example of the porous film of an inorganic material having a hydrophilic group can be a porous film containing a silica compound. A glass filter can be an example of the porous film having a silica compound. A porous silica thin film as described in Japanese Patent No. 3,058,342 can be an example of the glass filter. The porous silica thin film can be produced as follows. That is, a developing solution of a cationic amphipatic substance having the ability of forming a bimolecular film is developed on a board. Then, a solvent is removed from a liquid film on the board to thereby prepare a multilayer bimolecular thin film of the amphipatic substance. The multilayer bimolecular thin film is brought into contact with a solution containing a silica compound. Then, the multilayer bimolecular thin film is extracted and removed.

Examples of a method of introducing a hydrophilic group into a porous film of an inorganic material having no hydrophilic group include: a method of chemically bonding a porous film and a graft polymer chain to each other; and a method of polymerizing a graft polymer chain with a porous film as a stare point by using a monomer having a hydrophilic group having a double bond in a molecule.

To attach the porous film and the graft polymer chain attached to each other by chemical bonding, a functional group which can react with a functional group at a terminal of the graft polymer chain is introduced into an inorganic material and the graft polymer is chemically bonded thereto. To polymerize the graft polymer chain with the porous film as a start point by using a monomer having a hydrophilic group having a double bond in a molecule, a functional group which will serves as a start point for polymerizing the compound having a double bond is introduced into an inorganic material. A graft polymer having a hydrophilic group and a monomer having a hydrophilic group having a double bond in a molecule as described in the method of chemically bonding the graft polymer chain to the porous film of an organic material having no hydrophilic group can be preferably used as the graft polymer having a hydrophilic group and the monomer having a hydrophilic group having a double bond in a molecule.

As another method for introducing a hydrophilic group into the porous film of an inorganic material having no hydrophilic group, the porous film can be coated with a material having a hydrophilic group. The material used in coating is not particularly limited as long as it has a hydrophilic group concerned with adsorption of nucleic acid. A polymer of an organic material is preferred from the point of view of facilitation of operation. Examples of the polymer may include: polyhydroxyethyl acrylate, polyhydroxyethyl methacrylate, and salt thereof; polyvinyl alcohol, polyvinyl pyrrolidone, polyacrylic acid, polymethacrylic acid, and salt thereof; and polyoxyethylene, actyl cellulose, a mixture of acetyl celluloses different in acetyl value, and so on.

After the porous film of an inorganic material having no hydrophilic group is coated with acetyl cellulose or a mixture of acetyl celluloses different in acetyl value, the acetyl cellulose or the mixture of acetyl cellulose different in acetyl value for use in coating may be saponified. In this case, the saponification rate is preferably selected to be not lower than about 5%. Especially, the saponification rate is preferably selected to be not lower than about 10%.

An example of the porous film of an inorganic material having no hydrophilic group can be a porous film produced by processing a metal such as aluminum, ceramics such as glass, cement or pottery, or new ceramics, silicon, activated carbon, etc.

The cartridge for isolation and purification of nucleic acid is preferably formed so that other members than the nucleic acid-adsorbent porous film permeable to the aforementioned solution are stored in the container having at least two openings. Plastics such as polypropylene, polystyrene, polycarbonate, polyvinyl chloride, etc. may be used as the material of the container. A biodegradable material may be also preferably used. The container may be transparent or colored.

Cartridge for isolation and purification of a nucleic acid having means for identifying the cartridge individually can be used as the cartridge for isolation and purification of nucleic acid. A bar code, a magnetic tape, etc. may be used as the means for identifying the cartridge individually.

A cartridge having a structure in which the nucleic acid-adsorbent porous film can be easily taken out from the container having at least two openings may be also used.

The cartridge for isolation and purification of nucleic acid in which the nucleic acid-adsorbent porous film permeable to each solution can be used for isolating and purifying nucleic acid by the steps of:

(a) injecting a nucleic acid-containing specimen liquid into a container having at least two openings, through one opening of cartridge for isolation and purification of a nucleic acid containing a nucleic acid-adsorbent porous film permeable to a solution;

(b) pressurizing the inside of the cartridge for isolation and purification of nucleic acid by using a pressure difference generation device connected to one opening of the cartridge for isolation and purification of nucleic acid, and passing the injected nucleic acid-containing specimen liquid through the nucleic acid-adsorbent porous film, and discharging the nucleic acid-containing specimen liquid from the container through the other opening of the cartridge for isolation and purification of nucleic acid to thereby adsorb nucleic acid into the nucleic acid-adsorbent porous film;

(c) injecting a washing liquid into the container through one opening of the cartridge for isolation and purification of nucleic acid;

(d) pressurizing the inside of the cartridge for isolation and purification of nucleic acid by using the pressure difference generation device connected to one opening of the cartridge for isolation and purification of nucleic acid, and passing the injected washing liquid through the nucleic acid-adsorbent porous film, and discharging the washing liquid from the container through the other opening to thereby wash the nucleic acid-adsorbent porous film in a state in which nucleic acid is adsorbed on the nucleic acid-adsorbent porous film;

(e) injecting an elution liquid into the container through one opening of the cartridge for isolation and purification of nucleic acid; and (f) pressurizing the inside of the cartridge for isolation and purification of nucleic acid by using the pressure difference generation device connected to one opening of the cartridge for isolation and purification of nucleic acid, and passing the injected elution liquid through the nucleic acid-adsorbent porous film, and discharging the elution liquid from the container through the other opening to thereby desorb nucleic acid from the nucleic acid-adsorbent porous film and discharge the nucleic acid from the container of the cartridge for isolation and purification of nucleic acid.

In another embodiment, nucleic acid may be isolated and purified by the steps of:

(a) injecting a nucleic acid-containing specimen liquid into a container having at least two openings, through one opening of cartridge for isolation and purification of a nucleic acid containing a nucleic acid-adsorbent porous film permeable to a solution;

(b) reducing the pressure of the inside of the cartridge for isolation and purification of nucleic acid by using a pressure difference generation device connected to the other opening of the cartridge for isolation and purification of nucleic acid, and passing the injected nucleic acid-containing specimen liquid through the nucleic acid-adsorbent porous film, and discharging the nucleic acid-containing specimen liquid from the container through the other opening of the cartridge for isolation and purification of nucleic acid to thereby adsorb nucleic acid into the nucleic acid-adsorbent porous film;

(c) injecting a washing liquid into the container through one opening of the cartridge for isolation and purification of nucleic acid;

(d) reducing the pressure of the inside of the cartridge for isolation and purification of nucleic acid by using the pressure difference generation device connected to the other opening of the cartridge for isolation and purification of nucleic acid, and passing the injected washing liquid through the nucleic acid-adsorbent porous film, and discharging the washing liquid from the container through the other opening to thereby wash the nucleic acid-adsorbent porous film in a state in which nucleic acid is adsorbed on the nucleic acid-adsorbent porous film;

(e) injecting an elution liquid into the container through one opening of the cartridge for isolation and purification of nucleic acid; and (f) reducing the pressure of the inside of the cartridge for isolation and purification of nucleic acid by using the pressure difference generation device connected to the other opening of the cartridge for isolation and purification of nucleic acid, or applying centrifugal force on the cartridge for isolation and purification of nucleic acid, and passing the injected elution liquid through the nucleic acid-adsorbent porous film, and discharging the elution liquid from the container through the other opening to thereby desorb nucleic acid from the nucleic acid-adsorbent porous film and discharge the nucleic acid from the container of the cartridge for isolation and purification of nucleic acid.

In a further embodiment, nucleic acid may be isolated and purified by the steps of:

(a) injecting a nucleic acid-containing specimen liquid into a container having at least two openings, through one opening of cartridge for isolation and purification of a nucleic acid containing a nucleic acid-adsorbent porous film permeable to a solution;

(b) applying centrifugal force on the cartridge for isolation and purification of nucleic acid, and passing the injected nucleic acid-containing specimen liquid through the nucleic acid-adsorbent porous film, and discharging the nucleic acid-containing specimen liquid from the container through the other opening of the cartridge for isolation and purification of nucleic acid to thereby adsorb nucleic acid into the nucleic acid-adsorbent porous film;

(c) injecting a washing liquid into the container through one opening of the cartridge for isolation and purification of nucleic acid;

(d) applying centrifugal force on the cartridge for isolation and purification of nucleic acid, and passing the injected washing liquid through the nucleic acid-adsorbent porous film, and discharging the washing liquid from the container through the other opening to thereby wash the nucleic acid-adsorbent porous film in a state in which nucleic acid is adsorbed on the nucleic acid-adsorbent porous film;

(e) injecting an elution liquid into the container through one opening of the cartridge for isolation and purification of nucleic acid; and (f) applying centrifugal force on the cartridge for isolation and purification of nucleic acid, and passing the injected elution liquid through the nucleic acid-adsorbent porous film, and discharging the elution liquid from the container through the other opening to thereby desorb nucleic acid from the nucleic acid-adsorbent porous film and discharge the nucleic acid from the container of the cartridge for isolation and purification of nucleic acid.

The steps for isolating and purifying nucleic acid from a nucleic acid-containing specimen by using the cartridge for isolation and purification of nucleic acid including a container having at least two openings and a nucleic acid-adsorbent porous film stored in the container, and the pressure generation means may be preferably performed by an automatic apparatus for performing the steps automatically. In this manner, nucleic acid of a predetermined level can be obtained regardless of the operator's skill as well as the operation can be simplified and quickened.

The steps for isolating and purifying nucleic acid from a nucleic acid-containing specimen by using the cartridge for isolation and purification of nucleic acid and the pressure generation means will be described below with reference to an automatic nucleic acid extraction apparatus.

Figure 9:
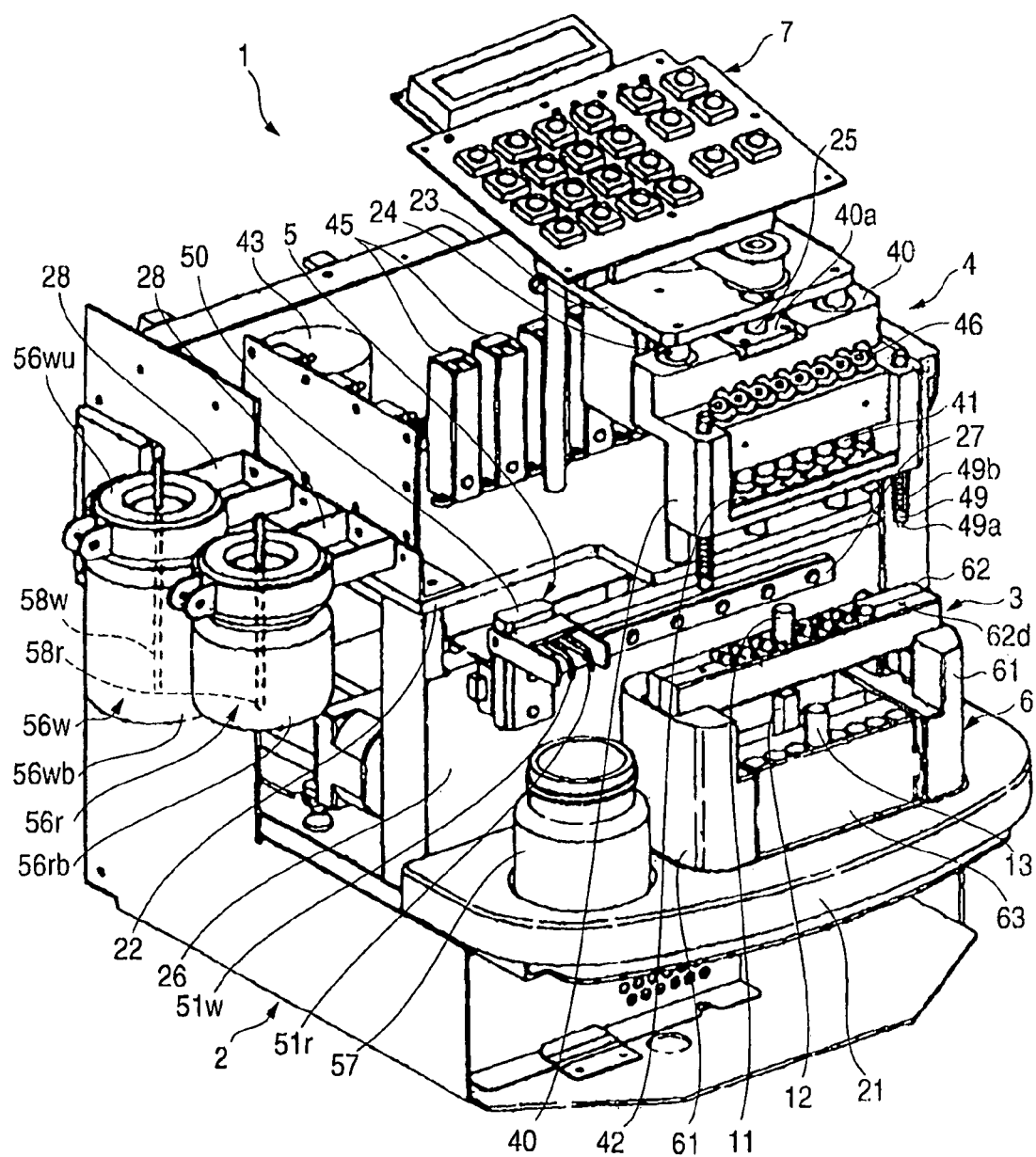
FIG. 9 is a perspective view showing an embodiment of a nucleic acid extraction apparatus in a state where a cover is removed.
Figure 10:
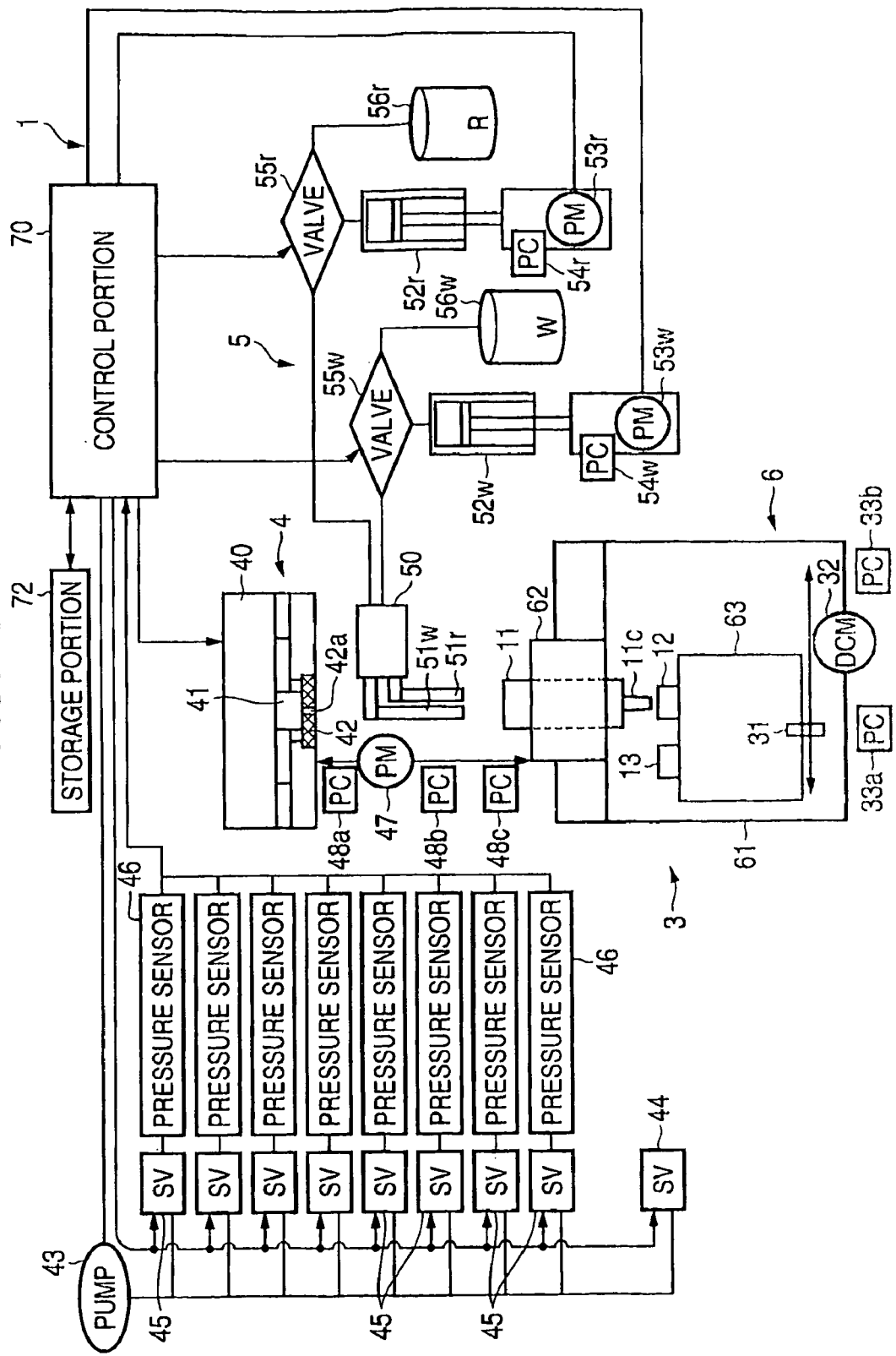
FIG. 10 is a schematic block diagram of the configuration of the nucleic acid extraction apparatus.

As shown in FIGS. 9 and 10, the automatic nucleic acid extraction apparatus 1 includes an apparatus body 2, a mount mechanism 3, a pressurized air supply mechanism 4, and a dispensing mechanism 5. The mount mechanism 3, the pressurized air supply mechanism 4 and the dispensing mechanism 5 are disposed in the apparatus body 2. The mount mechanism 3 holds a plurality of cartridges 11, a waste container 12 and a collection container 13. The pressurized air supply mechanism 4 introduces pressurized air into the cartridge for isolation and purification of nucleic acids 11. The dispensing mechanism 5 dispenses a washing liquid W and an elution liquid R into the cartridges 11. The mechanisms 3 to 5 will be described below specifically.

<Mount Mechanism>

The mount mechanism 3 has a mount table 21 in a front lower portion of the apparatus body 2. A rack 6 in which the plurality of cartridges 11, the waste container 12 and the collection container 13 are held is placed on the mount table 21. As also shown in FIG. 4, the rack 6 has a stand 61, a cartridge holder 62, and a container holder 63.

The stand 61 holds the cartridge holder 62 in pillar portions 61a on opposite sides so that the cartridge holder 62 can move up and down. The stand 61 holds the container holder 63 on a bottom plate 61b in a lower portion between the pillar portions 61a so that the container holder 63 can move back and forth.

Figure 14:
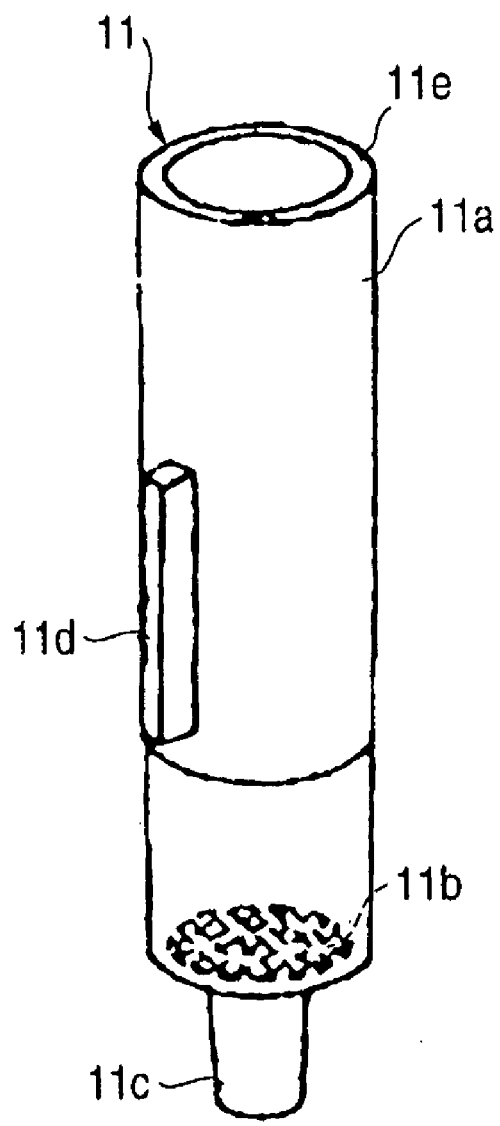
FIG. 14 is a perspective view of cartridge for isolation and purification of a nucleic acid.

The cartridge holder 62 is formed as a split-half structure in which front and rear plates are joined to each other. The cartridge holder 62 has a holding portion 62a extending horizontally, and support legs 62b extending vertically and disposed at opposite ends of the holding portion 62a. The support legs 62b are inserted into vertically extending slide grooves 61c of the pillar portions 61a of the stand 61 so that the support legs 62b can move up and down. The support legs 62b are urged upward by urging members (not shown) included in the stand 61. In the holding portion 62a, a plurality of holding holds. 62c are provided side by side. The cartridges 11 are inserted into the holding holes 62c from above. Lower ends of protrusions 11d (see FIG. 14) formed on opposite sides of cylindrical bodies 11a of the cartridges 11 are fitted and held into fitting members (not shown) in the cartridge holder 62. The fitting members are movable. To move the fitting members, fitting to the protrusions 11d is released so that all the cartridges 11 can be dropped down and discarded simultaneously.

Figure 11:
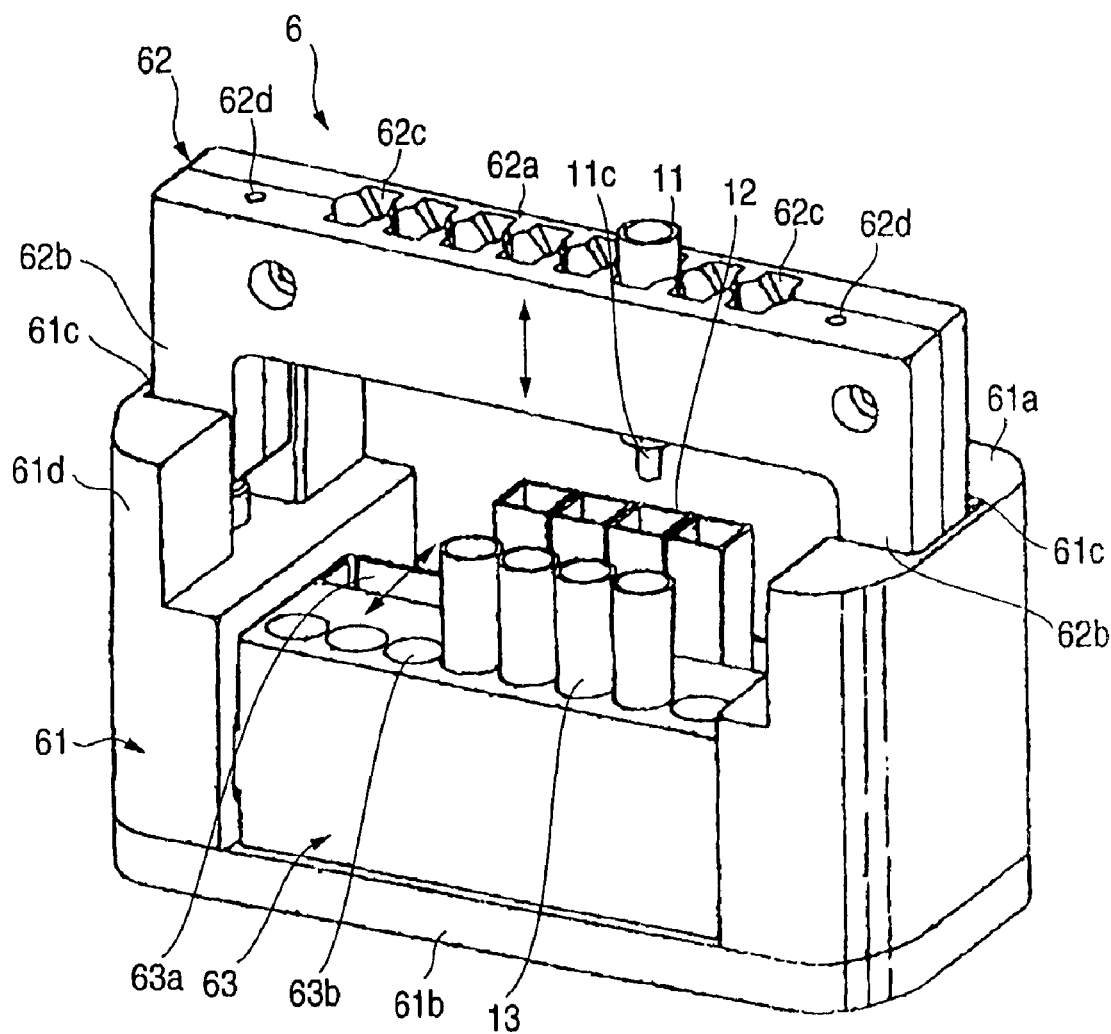
FIG. 11 is a perspective view of a rack in a mount mechanism.
Figure 12:
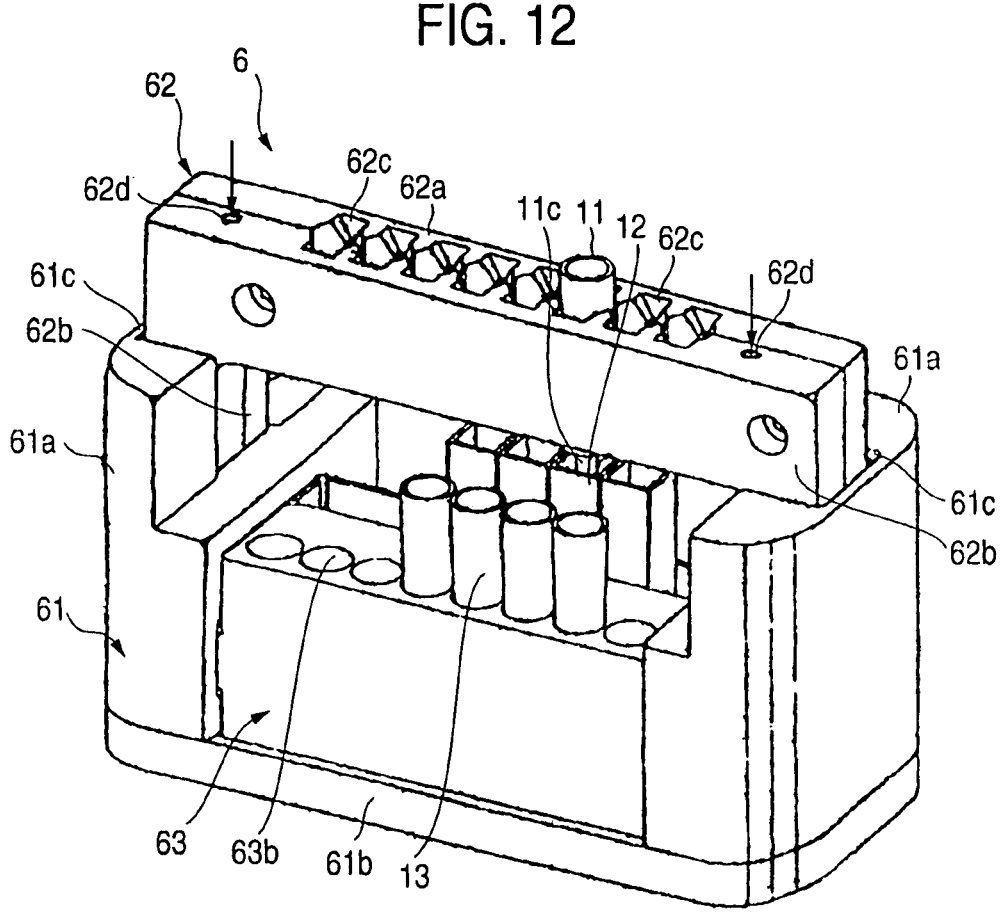
FIG. 12 is a perspective view showing a state of use of the rack.
Figure 13:
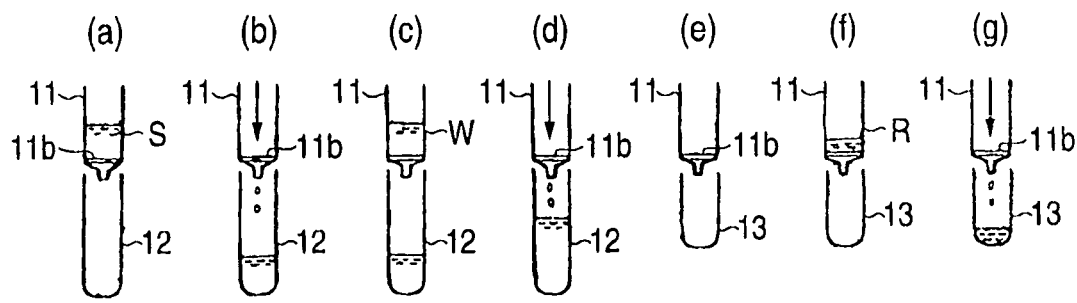
FIGS. 13(a) to 13(g) are a process view showing an extracting operation.

The cartridge holder 62 has pin holes 62d on opposite sides of its upper surface. In a condition of use, the cartridge holder 62 is pushed down while front ends 49a of pressure pins 49 (see FIG. 9) as alignment means which will be described later are fitted into the pin holes 62d respectively. In the position where the cartridge holder 62 is moved up as shown in FIG. 11, lower ends of discharge portions 11c of the cartridges 11 held in the cartridge holder 62 are located above the waste container 12 and the collection container 13 set in the container holder 63. When the cartridge holder 62 is moved down as shown in FIG. 12, setting is made so that the discharge portions 11c of the cartridges 11 are inserted by a predetermined value into the waste container 12 or the collection container 13.

The container holder 63 has waste container holding holes 63a and collection container holding holes 63b extending horizontally and arranged in two parallel rows. A plurality of waste containers 12 are held in the waste container holding holes 63a provided on the rear side so that the plurality of waste containers 12 can be arranged in a row. A plurality of collection containers 13 are held in the collection container holding holes 63b provided on the front side so that the plurality of collection containers 13 can be arranged in a row. The waste container holding holes 63a and the collection container holding holes 63b are arranged in positions equal to those of the holding holes 62c of the cartridge holder 62 and at equal intervals of a pitch equal to that of the holding holes 62c. The waste container holding holes 63a and the collection container holding holes 63b are set so that the waste containers 12 and the collection containers 13 are located below the held cartridges 11 respectively. To prevent confusion, it is preferable that the waste containers 12 are different in size, shape, etc. from the collection containers 13.

The container holder 63 is urged forward by an urging member not shown but included in the stand 61. The movement (back and forth movement) of the container holder 63 for exchanging the containers is performed in the condition that an operation member 31 (see FIG. 10) set on the mount table 21 is fitted into a fitting hole (not shown) of a bottom portion of the container holder 63 through an opening formed in the bottom plate 61b of the stand 61. The container holder 63 is moved back in accordance with the moving operation of the operation member 31 in accordance with the drive of a container exchange motor 32 (DC motor) so that the collection containers 13 are located below the cartridge holder 62. At the time of non-operation, the container holder 63 is urged by the urging member not shown so that the waste containers 12 are located below the cartridge holder 62. The operation of the container exchange motor 32 is controlled in accordance with detection by position sensors 33a and 33b.

<Pressurized Air Supply Mechanism>

As shown in FIGS. 9 and 10, the pressurized air supply mechanism 4 has a pressurizing head 40, a plurality of air nozzles 41, an air pump 43, a relief valve 44, on-off valves 45, and pressure sensors 46. The pressurizing head 40 can move up and down relative to the rack 6 of the mount mechanism 3. The plurality of air nozzles 41 (eight air nozzles in FIG. 9) are arranged in a row in the pressurizing head 40. The air pump 43 generates pressurized air. The on-off valves 45 are disposed in the air nozzles 41 respectively so that the air nozzles 41 can be opened and closed individually. The pressure sensors 46 are set in the air nozzles 41 respectively. Pressurized air is supplied to the cartridges 11 successively. The air pump 43, the relief valve 44 and the air nozzles 41 operate on the basis of a control instruction given from a control portion 70.

The pressurizing head 40 is held by guide rods 24 disposed vertically between an intermediate frame 22 and an upper frame 23 of the apparatus body 2 so that the pressurizing head 40 can move up and down. A ball nut 40a disposed in the pressurizing head 40 is thread-engaged with a ball screw 25 set vertically in the same manner as the guide rods 24. The pressurizing head 40 is controlled in accordance with detection by photo sensors 48a to 48c so that the pressurizing head 40 are moved up and down in accordance with the rotation of the ball screw 25 in accordance with the drive of an elevation motor 47 (pulse motor) through a timing belt and a pulley. Pressure pins 49 are provided on opposite sides of the pressurizing head 40. The pressure pins 49 are urged downward by springs 49b so that the pressure pins 49 can move up and down. Front ends 49a of the pressure pins 49 are fitted into the pin holes 62d in the upper surface of the cartridge holder 62 so that the pressure pins 49 presses the cartridge holder 62 while the positions of the front ends 49a are limited.

The pressure pins 49 are disposed to press the front position of the cartridge holder 62 so that the movement of the pressure pins 49 does not interfere with the horizontal movement of a washing liquid dispensing nozzle 51w and an elution liquid dispensing nozzle 51r (which will be described later) in the condition that the pressure pins 49 operate to press the cartridge holder 62.

The air nozzles 41 are disposed in the pressurizing head 40 so that the air nozzles 41 can move up and down individually while urged downward. A sheet-like sealing material 42 in which connection holes 42a (see FIG. 10) corresponding to the air nozzles 41 are opened is disposed below the air nozzles 41. When the pressurizing head 40 moves down, upper end openings of the cartridges 11 set in the cartridge holder 62 are pressed and closed by the front ends of the air nozzles 41 through the sealing material 42 so that pressurized air can be supplied into the cartridges 11 through the connection holes 42a.

The relief valve 44 is operated to open atmospheric air when air is discharged from passages between the air pump 43 and the on-off valves 45. An air circuit is formed so that the on-off valves 45 are selectively operated to be opened so that pressurized air can be introduced from the air pump 43 into the cartridges 11 through corresponding air nozzles 41. That is, suction flow passages 14 are formed between the air pump 43 and the cartridges 11. Pressurized air is supplied on the basis of an instruction given from the control portion 70. The pressure sensors 46 are disposed in the air nozzles 41 respectively and detect the pressures of the inside of the cartridges individually. The pressure sensors 46 cooperate with the control portion 70 to perform controlling for determining completion of discharge of liquid on the basis of the aforementioned algorithm in accordance with a pattern of pressure change.

<Dispensing Mechanism>

The dispensing mechanism 5 has a washing liquid dispensing nozzle 51w, an elution liquid dispensing nozzle 51r, a washing liquid supply pump 52w, an elution liquid supply pump 52r, and a waste bottle 57. The washing liquid dispensing nozzle 51w and the elution liquid dispensing nozzle 51r are disposed in a nozzle movement table 50 which can move horizontally on the rack 6. The washing liquid supply pump 52w supplies a washing liquid W stored in a washing liquid bottle 56w to the washing liquid dispensing nozzle 51w. The elution liquid supply pump 52r supplies an elution liquid R collected into an elution liquid bottle 56r to the elution liquid dispensing nozzle 51r. The waste bottle 57 is placed on the mount table 21.

The nozzle movement table 50 is held by a guide rail 27 set horizontally on a vertical wall 26 of the apparatus body 2 so that the nozzle movement table 50 can move horizontally. The movement of the nozzle movement table 50 is stopped on the cartridges 11 successively by a nozzle movement motor (pulse motor) not shown. For restoration, the drive of the nozzle movement table 50 is controlled so that the nozzle movement table 50 stops on the waste bottle 57. Each of the washing liquid dispensing nozzle 51w and the elution liquid dispensing nozzle 51r has a front end bent downward. The washing liquid dispensing nozzle 51w is connected to the washing liquid supply pump 52w through a change-over valve 55w. The washing liquid supply pump 52w is connected to the washing liquid bottle 56w through the change-over valve 55w. The elution liquid dispensing nozzle 51r is connected to the elution liquid supply pump 52r through a change-over valve 55r. The elution liquid supply pump 52r is connected to the elution liquid bottle 56r through the change-over valve 55r. The washing liquid bottle 56w and the elution liquid bottle 56r are disposed on a side of the apparatus body 2. The washing liquid supply pump 52w and the elution liquid supply pump 52r are formed as syringe pumps respectively. Pump motors 53w and 53r (pulse motors) control to drive piston members of the syringe pumps so that a predetermined amount of washing liquid W and a predetermined amount of elution liquid R can be dispensed on the basis of position detection by sensors 54w and 54r respectively. These pump motors 53w and 53r and change-over valves 55w and 55r operate on the basis of an instruction given from the control portion 70.

To dispense the washing liquid W or the elution liquid R, the change-over valve 55w or 55r is switched to the washing liquid bottle 56w side or the elution liquid bottle 56r side to drive the pump motor 53w or 53r to move back the piston member of the washing liquid supply pump 52w or the elution liquid supply pump 52r. As a result, the washing liquid W or the elution liquid R is sucked and stored into the washing liquid supply pump 52w or the elution liquid supply pump 52r. Succeedingly, the change-over valve 55w or 55r is switched to the washing liquid dispensing nozzle 51w side or the elution liquid dispensing nozzle 51r side to drive the motor pump 53w or 53r to push in the piston member of the washing liquid supply pump 52w or the elution liquid supply pump 52r. After the washing liquid or the elution liquid is discharged from the washing liquid dispensing nozzle 51w or the elution liquid dispensing nozzle 51r to the waste bottle 57 until air in the passage is exhausted, the drive of the washing liquid supply pump 52w or the elution liquid supply pump 52r is stopped. Then, the washing liquid dispensing nozzle 51w or the elution liquid dispensing nozzle 51r is moved on the cartridges 11. While the quantity of drive of the washing liquid supply pump 52w or the elution liquid supply pump 52r is controlled, a predetermined amount of the washing liquid W or the elution liquid R is dispensed into each cartridge 11.

Each of the washing liquid bottle 56w and the elution liquid bottle 56r has a container body 56wb or 56rb, and a cap 56wu or 56ru. Slim pipe-like suction tubes 58w and 58r are disposed in the caps 56wu and 56ru respectively. Lower ends of the suction tubes 58w and 58r are opened near bottom portions of the container bodies 56wb and 56rb so that the washing liquid W or the elution liquid R can be sucked up in accordance with the operation of the washing liquid supply pumps 52w worth elution liquid supply pump 52r.

The mechanisms 3 to 5 are controlled to be driven on the basis of a program stored in advance in a storage portion 72 connected to the control portion 70, by the control portion 70 associated with an input operation of an operation panel 7 disposed in the upper portion of the apparatus body 2.

An operation of extraction by the nucleic acid extraction apparatus 1 will be described specifically. First, the cartridges 11 are set in the cartridge holder 62 in the rack 6 of the mount mechanism 3. The waste containers 12 and the collection containers 13 are set in the container holder 63 in the rack 6 of the mount mechanism 3. The rack 6 is placed on the mount table 21 of the apparatus body 2 to perform preparation. Then, a specimen liquid S subjected to dissolving treatment is injected into the cartridges 11 successively by a pipette or the like. Incidentally, the specimen liquid S may be injected into the cartridges 11 after or before the cartridges 11 are set in the rack 6 before the rack 6 is mounted in the apparatus 1.

When the apparatus is then operated by the operation of the operation panel 7, the pressurizing head 40 moves clown by the drive of the elevation motor 47 of the pressurized air supply mechanism 4 so that the front ends 49a of the pressure pins 49 are fitted into the pin holes 62d of the cartridge holder 62 and press and move down the cartridge holder 62 to limit the position of the cartridge holder 62. At the same time, a lower end discharge portion 11c of a cartridge 11 is inserted by a predetermined quantity into a waste container 12 as shown in FIG. 12 so that contamination with the discharged liquid leaked out by scattering or the like can be prevented. The pressurizing head 40 further moves down so that the lower end portion of each air nozzle 41 comes into pressure contact with the upper end opening of the cartridge 11 through the sealing material 42 to thereby close the upper end opening of the cartridge 11. On this occasion, because the position of the cartridge holder 62 is limited by the pressure pins 49, the air nozzles 41 can come into pressure contact with the cartridges 11 respectively accurately to attain sure closure.

Then, pressurized air is supplied. The air pump 43 is driven on the basis of an instruction given from the control portion 70 in the condition that all the on-off valves 45 are closed. The first on-off valve 45 is opened. A predetermined amount of pressurized air is supplied from the air pump 43 to the first cartridge 11 through the first air nozzle 41.

Then, the first on-off valve 45 is closed and the second on-off valve 45 is opened. Pressurized air is supplied to the second cartridge 11 through the second air nozzle 41. This operation is repeated successively so that pressure is applied on all the cartridges 11. When the specimen liquid S on which pressure acts passes through the nucleic acid-adsorbent porous film 11b, nucleic acid is adsorbed and held on the nucleic acid-adsorbent porous film 11b. Other liquid components than nucleic acid are discharged from the discharge portion 11c of the lower portion to the waste container 12. When all the specimen liquid S passes through the nucleic acid-adsorbent porous film 11b, pressure change as shown in FIGS. 2A to 2C, 4A to 4C and 6A to 6C occurs. When the pressure change is detected, completion of discharge of liquid is determined. In this manner, when completion of extraction in all the cartridges 11 is detected by the pressure sensors 46, the pressurizing head 40 is moved up.

Then, processing is shifted to washing treatment. The up movement of the pressurizing head 40 after supply of the pressurized air is performed while the state shown in FIG. 12 is kept, that is, while the state where the air nozzle 41 is departed from the cartridge 11 and stopped in the position where the air nozzle 41 is moved up to a height allowing the nozzle movement table 50 to move, the pressure pins 49 press the cartridge holder 62 and the lower end of the cartridge 11 is inserted into the waste container 12. Then, the nozzle movement table 50 is moved. The washing liquid dispensing nozzle 51w is stopped on the first cartridge 11. A predetermined amount of the washing liquid W is dispensed into the first cartridge 11. The nozzle movement table 50 is moved to the next cartridge 11 so that the washing liquid W is dispensed into the cartridges 11 successively. When dispensing of the washing liquid W into all the cartridges 11 is completed, the pressuring head 40 moves down. After the lower end portion of each air nozzle 41 comes into pressure contact with the upper end opening of a corresponding cartridge 11 through the sealing material 42 to close the upper end opening, the on-off valves 45 are operated successively in the same manner as described above. Thus, pressurized air is supplied into the cartridges 11 in the same manner as described above. The washing solution W on which pressure acts passes through the nucleic acid-adsorbent porous film 11b to thereby wash and remove other impurities than nucleic acid. The washing liquid W is discharged from the discharge portion 11c of the lower portion to the waste container 12. When the washing liquid W in all the cartridges 11 is discharged after passage through the nucleic acid-adsorbent porous film 11b, the pressurizing head 40 is moved up to the initial position. When the washing treatment needs to be performed several times, the aforementioned operation is repeated.

Then, processing is shifted to collecting treatment. First, the pressure pins 49 move up in accordance with the up movement of the pressurizing head 40 after the washing treatment, so that the cartridge holder 62 of the rack 6 also moves up. After the lower end discharge portion 11c of the cartridge 11 moves up with respect to the waste container 12, the operation member 31 of the mount mechanism 3 is operated to move back the container holder 63. The collection container 13 located below the cartridge 11 is exchanged.

Then, the pressurizing head 40 moves down. The front ends of the pressure pins 49 are fitted into the pin holes 62d of the cartridge holder 62 to press the cartridge holder 62. In this manner, the state where the lower end of the cartridge 11 is inserted into the collection container 13 is kept. Then, the nozzle movement table 50 is moved. The elution liquid dispensing nozzle 51r is stopped on the first cartridge 11. A predetermined amount of the elution liquid R is dispensed into the first cartridge 11. The nozzle movement table 50 is moved to the next cartridge 11 so that the elution liquid R is dispensed into the cartridges 11 successively. When dispensing of the elution liquid R into all the cartridges 11 is completed, the pressuring head 40 moves down in the same manner as described above. After the lower end portion of each air nozzle 41 is brought into pressure contact with the upper end opening of the cartridge 11 through the sealing material 42 to close the upper end opening, the on-off valves 45 are opened successively. Thus, pressurized air is supplied into the cartridges 11 successively in the same manner as described above. The elution liquid R on which pressure acts passes through the nucleic acid-adsorbent porous film 11b to thereby desorb nucleic acid adsorbed on the nucleic acid-adsorbent porous film 11b. Thus, nucleic acid is discharged together with the elution liquid R from the discharge portion 11C of the lower portion to the collection container 13. When the elution liquid R in all the cartridges 11 is discharged to the collection containers 13, the pressurizing head 40 is moved up. Thus, a series of operations is completed.

After the extracting operation is completed, the rack 6 is removed from the mount table 21. The cartridges 11 and the waste containers 12 are taken out from the cartridge holder 62 and the container holder 63 and discarded. On the other hand, the collection containers 13 are taken out from the container holder 63, covered if necessary, and subjected to the next nucleic acid analyzing treatment.

Although this embodiment has shown the case where a plurality of cartridge for isolation and purification of nucleic acids 11 are mounted, the invention is not limited thereto. For example, the invention may be applied to the case where only one cartridge for isolation and purification of nucleic acid 11 is mounted.

Any gas may be used as air supplied from the air pump 43 to the cartridge for isolation and purification of nucleic acid 11 as long as the gas has no influence on the property of the liquid 16.

INDUSTRIAL APPLICABILITY

According to the invention, when a liquid is injected into a container having a nucleic acid-adsorbent solid phase stored therein and is discharged from the container through the nucleic acid-adsorbent solid phase by a pressure difference generated between the inside and outside of the container, completion of discharge of the liquid can be automatically determined accurately and rapidly regardless of the difference in kind of the nucleic acid-adsorbent solid phase stored in the container, the difference in production lot of the nucleic acid-adsorbent solid phase, the difference in production lot of the container per se, the difference in the container in each production lot, the kind of the liquid to be used, and so on. Accordingly, in automation of the nucleic acid isolation and purification steps using the nucleic acid-adsorbent solid phase excellent in isolating performance, efficiency can be improved so greatly that take time can be shortened and that the throughput of isolation and purification can be improved greatly.

The invention claimed is:

1. A method of automatically isolating and purifying nucleic acid from a nucleic acid-containing specimen, the method comprises:
   a) injecting a liquid into a cartridge for isolation and purification of a nucleic acid including at least two openings from one opening of the at least two openings, in which the cartridge includes a container having the at least two openings and containing a nucleic acid-adsorbent solid phase;
   b) passing the liquid through the nucleic acid-adsorbent solid phase by a pressure difference generated by a pressure generation means for generating a pressure difference between the inside and outside of the container; wherein a pressure generated in the inside of the container by the pressure generation means is measured and a pressure change velocity and a pressure change acceleration are calculated on the basis of the value of the measured pressure, and
   c) discharging the liquid from the other opening of the container to the outside of the container by a pressure difference generated by the pressure generation means, wherein the timing of completion of discharge of the liquid from the container is determined by use of a temporal change pattern of a measured pressure selected from the group consisting of
   (1) when the pressure of the inside of the container reaches a set value in the middle of pressurizing the inside of the cartridge by the pressure generation means, the pressurization by the pressure generation means is stopped, and a point of time when the pressure change acceleration in said container is minimized after the stop of pressurization is determined as the timing of completion of discharge of the liquid from the container;
   (2) when the pressure of the inside of the container does not reach a set value in the middle of pressurizing the inside of the cartridge by the pressure generation means, at least one of a point of time when the pressure in the container is maximized and the pressure change velocity in the container becomes zero or less and a point of time when the pressure in the container is maximized and the pressure change acceleration in the container is minimized, is determined as the timing of completion of discharge of the liquid from the container; and
   (3) when the pressure of the inside of the container does not reach a set value and is not maximized in the middle of pressurizing the inside of the cartridge by the pressure generation means, a point of time when the pressure change velocity in the container becomes lower than a threshold value, is determined as the timing of completion of discharge of the liquid from the container.

2. The method according to claim 1, which comprises:
   (1) injecting and pressurizing a nucleic acid-containing specimen liquid into the container through one of the at least two openings, and discharging the nucleic acid-containing specimen liquid from the other opening to thereby adsorb a nucleic acid contained in the nucleic acid-containing specimen liquid to the nucleic acid-adsorbent solid phase;
   (2) dispensing and pressurizing a washing liquid into the container through one of the at least two openings, and discharging the washing liquid from the container through the other opening to remove impurities; and
   (3) dispensing and pressurizing an elution liquid into the container through one of the at least two openings to isolate and discharge the nucleic acid adsorbed to the nucleic acid-adsorbent solid phase from the container through the other opening together with the elution liquid to thereby collect nucleic acid.

3. The method according to claim 2, wherein in response of the determined timing of completion of discharge of the liquid, the subsequent step is performed.

* * * * *